US012636098B2

(12) United States Patent
Pandya et al.

(10) Patent No.: US 12,636,098 B2
(45) Date of Patent: May 26, 2026

(54) SYSTEMS AND METHODS FOR DETECTING, LOCALIZING, ASSESSING, AND VISUALIZING BLEEDING IN A SURGICAL FIELD

(71) Applicants: Wayne State University, Detroit, MI (US); RediMinds, Inc., Southfield, MI (US)

(72) Inventors: Abhilash K. Pandya, Grosse Ile, MI (US); Mostafa Daneshgar Rahbar, Dearborn Heights, MI (US); Luke A. Reisner, Madison Heights, MI (US); Hao Ying, Novi, MI (US); Mahendra Bhandari, Novi, MI (US); Madhusudhan Reddiboina, Southfield, MI (US)

(73) Assignees: Wayne State University, Detroit, MI (US); RediMinds, Inc., Southfield, IL (US)

( * ) Notice: Subject to any disclaimer, the term of this patent is extended or adjusted under 35 U.S.C. 154(b) by 424 days.

(21) Appl. No.: 18/028,130

(22) PCT Filed: Sep. 22, 2021

(86) PCT No.: PCT/US2021/051590
§ 371 (c)(1),
(2) Date: Mar. 23, 2023

(87) PCT Pub. No.: WO2022/066797
PCT Pub. Date: Mar. 31, 2022

(65) Prior Publication Data
US 2023/0363836 A1 Nov. 16, 2023

Related U.S. Application Data

(60) Provisional application No. 63/082,459, filed on Sep. 23, 2020.

(51) Int. Cl.
*G06T 7/00* (2017.01)
*A61B 5/02* (2006.01)
(Continued)

(52) U.S. Cl.
CPC .......... *A61B 34/30* (2016.02); *A61B 5/02042* (2013.01); *G06T 7/0016* (2013.01);
(Continued)

(58) Field of Classification Search
CPC .......... G06T 2207/10024; G06T 2207/10016; G06T 2207/10068; G06T 7/11;
(Continued)

(56) References Cited

U.S. PATENT DOCUMENTS 10,758,309 B1* 9/2020 Chow ............ A61B 17/320016
2007/0230930 A1 10/2007 Chang
(Continued)

OTHER PUBLICATIONS

International Search Report and Written Opinion for PCT Application No. PCT/US2021/051590, mailed Dec. 10, 2021, 13 pages.
(Continued)

*Primary Examiner* — Li Liu
(74) *Attorney, Agent, or Firm* — Tanya Harding; C. Rachael Winger; Lee & Hayes PC

(57) ABSTRACT

Various systems, methods, and devices for identifying intra-operative bleeding are described. An example method includes identifying a first frame depicting a surgical scene; identifying a second frame depicting the surgical scene; identifying whether the second frame depicts bleeding by analyzing the first frame and the second frame; and outputting the second frame with an augmentation indicating whether bleeding is depicted in the second frame.

20 Claims, 16 Drawing Sheets

(51) Int. Cl.
    *A61B 34/30*         (2016.01)
    *A61B 90/00*         (2016.01)
(52) U.S. Cl.
    CPC .................. *A61B 2090/365* (2016.02); *G06T 2207/10016* (2013.01); *G06T 2207/10024* (2013.01); *G06T 2207/20081* (2013.01)
(58) Field of Classification Search
    CPC ....... G06T 7/0016; G06T 7/0012; G06T 7/90; G06T 2200/24; A61B 5/02042; A61B 90/361; A61B 34/30; A61B 90/37; A61B 1/00055; A61B 34/25; A61B 1/00045; A61B 2090/365; A61B 5/743
    See application file for complete search history.

(56) References Cited

U.S. PATENT DOCUMENTS

| | | | | |
|---|---|---|---|---|
| 2012/0138658 | A1 | 6/2012 | Ullrich et al. | |
| 2012/0157820 | A1 | 6/2012 | Zhang et al. | |
| 2012/0316421 | A1* | 12/2012 | Kumar | A61B 1/000096 |
| | | | | 600/407 |
| 2018/0125333 | A1 | 5/2018 | Zhao et al. | |
| 2018/0247560 | A1* | 8/2018 | Mackenzie | A61B 90/361 |
| 2019/0110856 | A1* | 4/2019 | Barral | A61B 90/37 |
| 2020/0265273 | A1 | 8/2020 | Wei et al. | |
| 2021/0142487 | A1* | 5/2021 | Xu | A61B 34/20 |
| 2021/0216822 | A1* | 7/2021 | Paik | G06F 3/167 |
| 2021/0321887 | A1* | 10/2021 | Fukazawa | G06T 7/246 |

OTHER PUBLICATIONS

Boulougoura, et al., "Intelligent Systems For Computer-Assisted Clinical Endoscopic Image Analysis," Proceedings of the second IASTED international conference on biomedical engineering, Acta Press, 2004, pp. 405-408.
Castillo, et al., "Laparoscopic Repair of an Iliac Artery Injury During Radical Cystoprostatectomy," Surgical Laparoscopy, Endoscopy & Percutaneous Techniques, vol. 18, No. 3, 2008, pp. 315-318.
Dabass, et al., "Mammogram Image Enhancement Using Entropy and CLAHE Based Intuitionistic Fuzzy Method," 2019 6th International Conference on Signal Processing and Integrated Networks (SPIN), 2019, pp. 24-29.
Fang and Zhao, "A hybrid active contour model based on global and local information for medical image segmentation," Multidimensional Systems and Signal Processing, vol. 30, 2019, pp. 689-703.
Fu, "Computer-Aided Bleeding Detection in WCE Video," IEEE Journal of Biomedical and Health Informatics, vol. 18, No. 2, 2014, pp. 636-642.
Garisto, et al., "Robot-Assisted Single Port Partial Nephrectomy Using The Sp Surgical System: First Clinical Experience," The Journal of Urology, vol. 201, No. 4S, 2019, pp. e848.
German, et al., "Entropy-based image merging," Proceedings of the Second Canadian Conference on Computer and Robot Vision (CRV'05), 2005, pp. 81-86.
Hwang, et al., "Blood Detection in Wireless Capsule Endoscopy using Expectation Maximization Clustering," Proc. of SPIE, vol. 6144, 2006, pp. 1-11.
Ishihara, et al., "Infrared endoscopic system for bleeding-point detection after flushing with indocyanine green solution," Gastrointestinal Endoscopy, vol. 68, No. 5, 2008, pp. 975-981.
Jung, et al., "Active Blood Detection in a High Resolution Capsule Endoscopy using Color Spectrum Transformation," 2008 International Conference on BioMedical Engineering and Informatics, 2008, pp. 859-862.
Lau and Correia, "Detection of bleeding patterns in WCE video using multiple features," Proceedings of the 29th Annual International Conference of the IEEE EMBS, 2007, pp. 5601-5604.

Li and Meng, "Computer Aided Detection Of Bleeding In Capsule Endoscopy Images," 2008 Canadian Conference on Electrical and Computer Engineering, 2008, pp. 001963-001966.
Li and Meng, "Computer-Aided Detection of Bleeding Regions for Capsule Endoscopy Images," IEEE Transactions on Biomedical Engineering, vol. 56, No. 4, 2009, pp. 1032-1039.
Liu and Yuan, "Obscure bleeding detection in endoscopy images using support vector machines," Optimization and Engineering, vol. 10, 2009, pp. 289-299.
Mackiewicz, et al., "Bleeding Detection in Wireless Capsule Endoscopy using adaptive colour histogram model and Support Vector Classification," Medical Imaging 2008: Image Processing, Proc. of SPIE, vol. 6914, 2008, pp. 1-12.
Makihara, et al., "Object Recognition Supported by User Interaction for Service Robots," 2002 International Conference on Pattern Recognition, vol. 3, 2002, pp. 561-564.
Pan, et al., "Bleeding Detection in Wireless Capsule Endoscopy Based on Probabilistic Neural Network," Journal of Medical Systems, vol. 35, 2011, pp. 1477-1484.
Pan, et al., "BP neural network classification for bleeding detection in wireless capsule endoscopy," Journal of Medical Engineering & Technology, vol. 33, No. 7, 2009, pp. 575-581.
Penna, et al., "A Technique For Blood Detection In Wireless Capsule Endoscopy Images," 17th European Signal Processing Conference, 2009, pp. 1864-1868.
Rahbar, et al., "An entropy-based approach to detect and localize intraoperative bleeding during minimally invasive surgery", vol. 16, No. 6, 2020, pp. 1-9.
Schäfer, et al., "A Nation's Experience of Bleeding Complications during Laparoscopy," The American Journal of Surgery, vol. 180, No. 1, 2000, pp. 73-77.
Skilling and Bryan, "Maximum entropy image reconstruction: general algorithm," Royal Astronomical Society, vol. 211, No. 1, 1984, pp. 111-124.
Search Report for European Application No. 21873369.9, Dated Sep. 20, 2024, 10 pages.
Talab, et al. "Management Of Intraoperative Complications During Robotic Renal And Ureteral Oncologic Surgery: The Lessons We Learned," The Journal Of Urology, vol. 201, No. 4S, 2019, pp. e851.
Wu, et al., "Local Shannon entropy measure with statistical tests for image randomness," Information Sciences, vol. 222, 2013, pp. 323-342.
Yan, et al., "Local entropy-based transition region extraction and thresholding," Pattern Recognition Letters, vol. 24, No. 16, 2003, pp. 2935-2941.
Zhang, et al., "Prevention and management of hemorrhage during a laparoscopic colorectal surgery," Annals of Laparoscopic and Endoscopic Surgery, vol. 1, No. 40, 2016, pp. 1-6.
Zong, et al., "Automatic ultrasound image segmentation based on local entropy and active contour model," Computers and Mathematics with Applications, vol. 78, 2019, pp. 929-943.
Al-Rahayfeh, et al., "Detection of Bleeding in Wireless Capsule Endoscopy Images Using Range Ration Color," The International Journal of Multimedia & Its Applications, vol. 2, No. 2, 2010, pp. 1-10.
Barros, "Vascular injuries during gynecological laparoscopy—the vascular surgeon's advice," Sao Paulo Med J., vol. 123, No. 1, 2005, pp. 38-41.
Bourbakis, et al., "A Neural Network-based Detection of Bleeding in sequences of WCE images," Proceedings of the 5th IEEE Symposium on Bioinformatics and Bioengineering, 2005, 4 pages.
Jaiswal, et al., "Morphological Method, PCA and LDA With Neural Networksface Recognition," Journal of Global Research in Computer Science, vol. 2, No. 6, 2011, pp. 35-48.
Kaushik, "Bleeding complications in laparoscopic cholecystectomy: Incidence, mechanisms, prevention and management," J Minim Access Surg., vol. 6, No. 3, 2010, pp. 59-65.
Khosravi, "A Pixon-based Image Segmentation Method Considering Textural Characteristics of Image," Journal of AI and Data Mining, vol. 7, No. 1, 2019, pp. 27-34.

(56)        References Cited

OTHER PUBLICATIONS

Michalak & Okarma, "Improvement of Image Binarization Methods Using Image Preprocessing with Local Entropy Filtering for Alphanumerical Character Recognition Purposes," Entropy, vol. 21, No. 562, 2019, pp. 1-18.
Otsu, "A Threshold Selection Method from Gray-Level Histograms," IEEE Transactions on Systems, Man, and Cybernetics, vol. 9, No. 1, 1979, pp. 62-66.

* cited by examiner

MODIFIED SECOND FRAME 400

RED PIXEL REGION(S) 402

BOUNDARY 404

BLEEDING INDICATOR

600

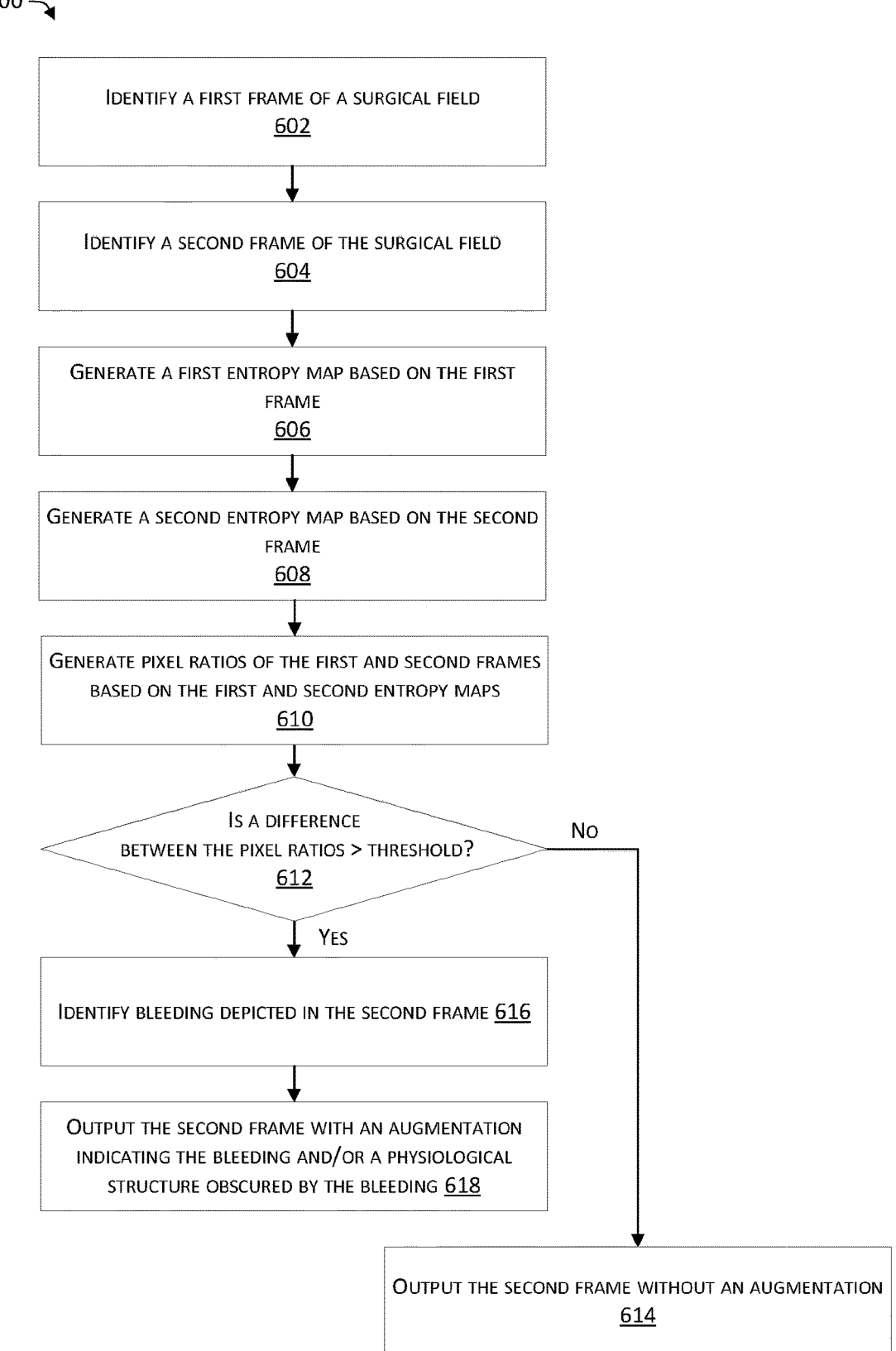

IDENTIFY A FIRST FRAME OF A SURGICAL FIELD
602

IDENTIFY A SECOND FRAME OF THE SURGICAL FIELD
604

GENERATE A FIRST ENTROPY MAP BASED ON THE FIRST
FRAME
606

GENERATE A SECOND ENTROPY MAP BASED ON THE SECOND
FRAME
608

GENERATE PIXEL RATIOS OF THE FIRST AND SECOND FRAMES
BASED ON THE FIRST AND SECOND ENTROPY MAPS
610

IS A DIFFERENCE
BETWEEN THE PIXEL RATIOS > THRESHOLD?
612

No

YES

IDENTIFY BLEEDING DEPICTED IN THE SECOND FRAME 616

OUTPUT THE SECOND FRAME WITH AN AUGMENTATION
INDICATING THE BLEEDING AND/OR A PHYSIOLOGICAL
STRUCTURE OBSCURED BY THE BLEEDING 618

OUTPUT THE SECOND FRAME WITHOUT AN AUGMENTATION
614

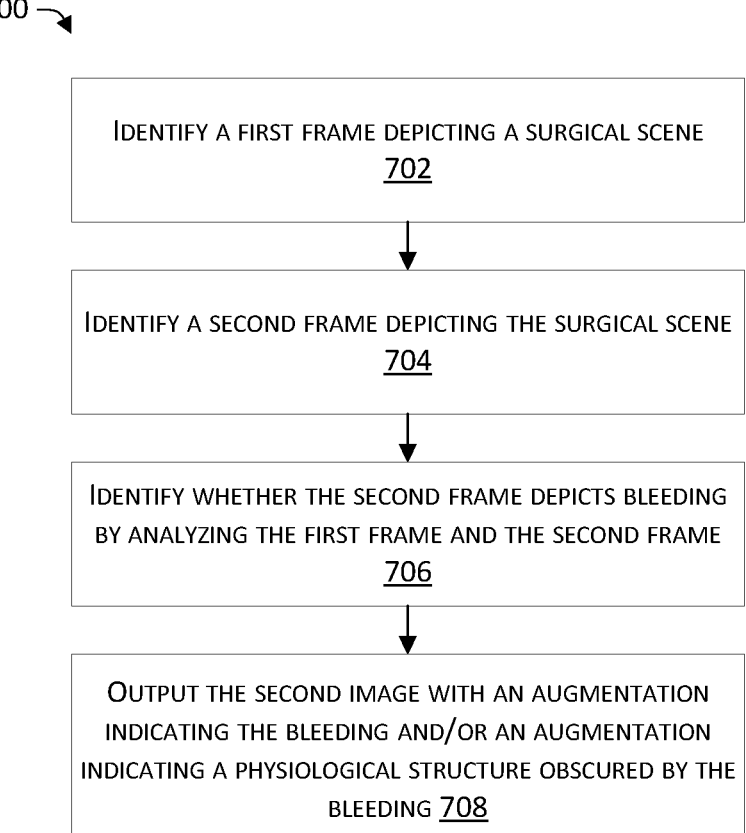

IDENTIFY A FIRST FRAME DEPICTING A SURGICAL SCENE
702

IDENTIFY A SECOND FRAME DEPICTING THE SURGICAL SCENE
704

IDENTIFY WHETHER THE SECOND FRAME DEPICTS BLEEDING
BY ANALYZING THE FIRST FRAME AND THE SECOND FRAME
706

OUTPUT THE SECOND IMAGE WITH AN AUGMENTATION
INDICATING THE BLEEDING AND/OR AN AUGMENTATION
INDICATING A PHYSIOLOGICAL STRUCTURE OBSCURED BY THE
BLEEDING 708

FIG. 7

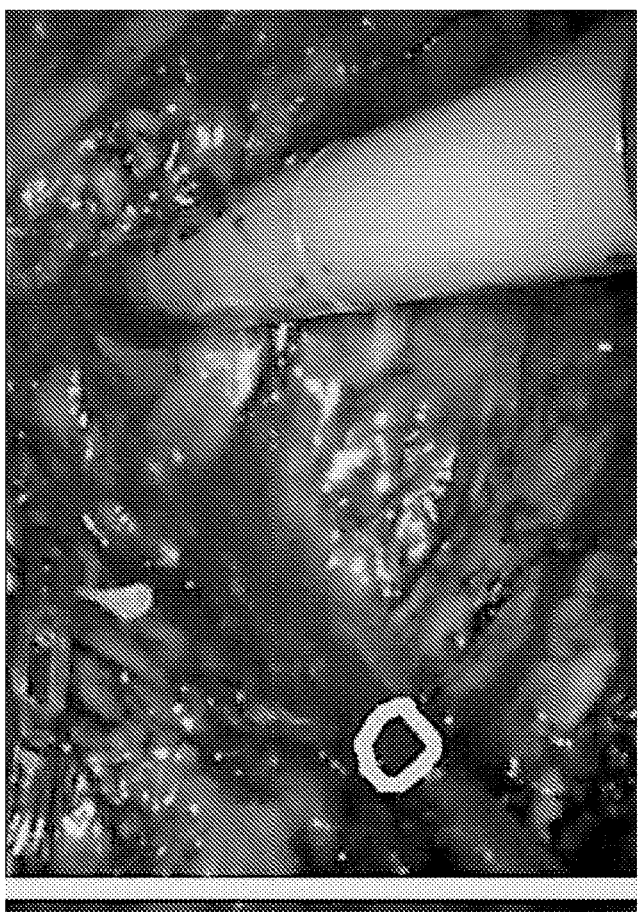
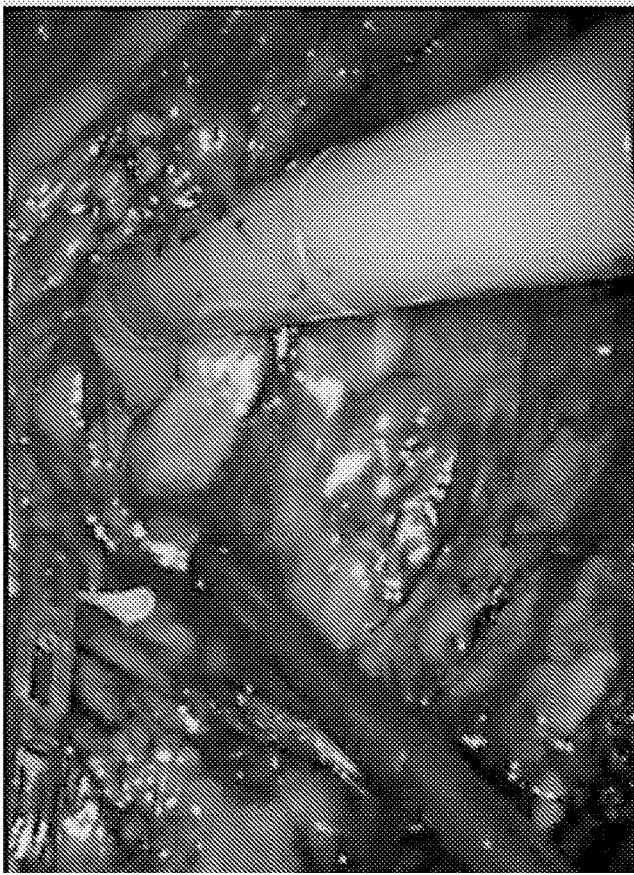
FIG. 10B

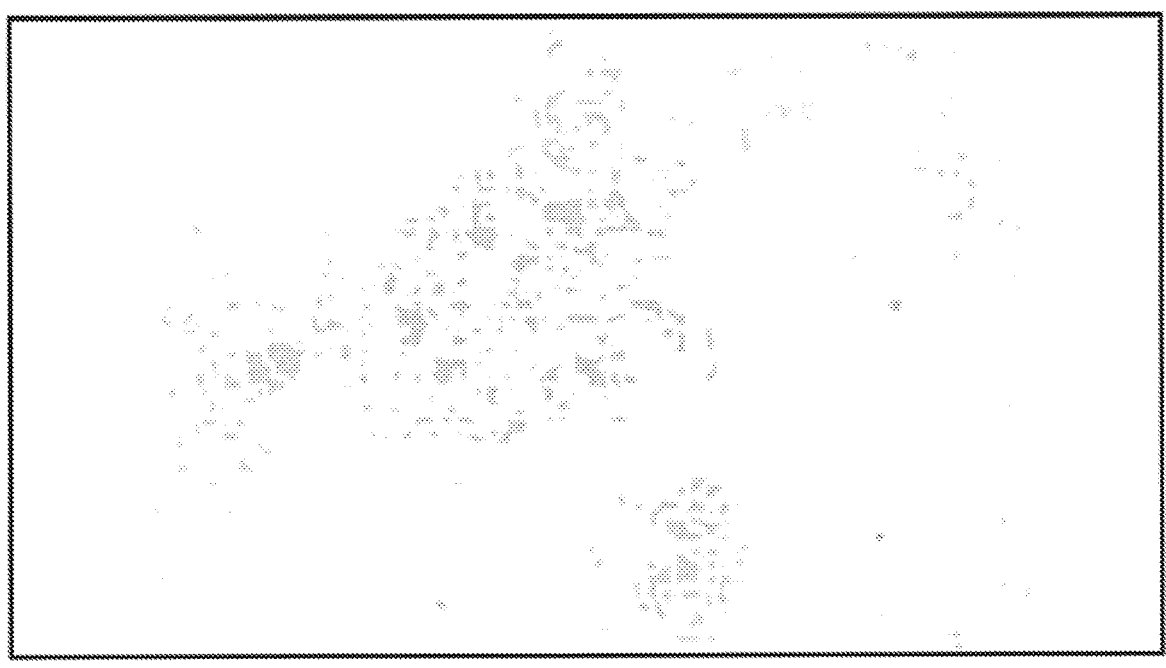
FIG. 12

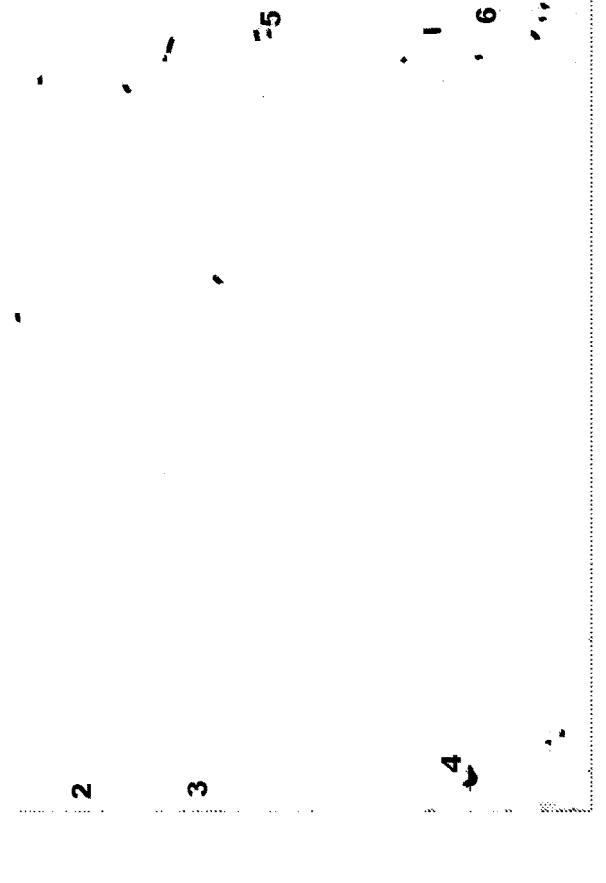
FIG. 13

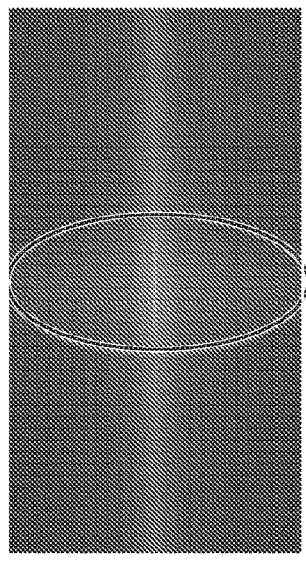
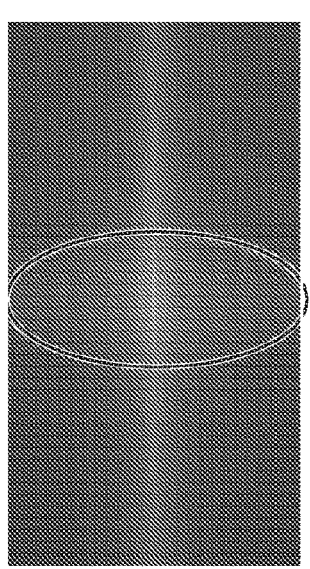
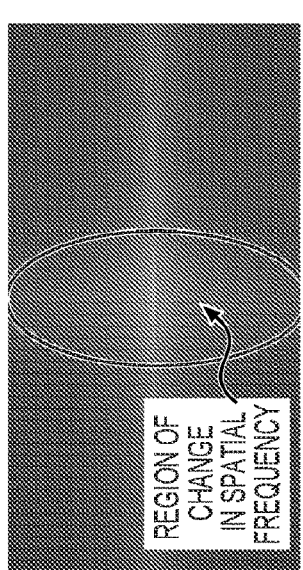
REGION OF CHANGE IN SPATIAL FREQUENCY
FIG. 15

SYSTEMS AND METHODS FOR DETECTING, LOCALIZING, ASSESSING, AND VISUALIZING BLEEDING IN A SURGICAL FIELD

CROSS-REFERENCE TO RELATED APPLICATIONS

This application is a U.S. National Phase Application based on International Patent Application No. PCT/US2021/051590, filed on Sep. 22, 2021, which claims the priority to and the benefit of U.S. Provisional Application No. 63/082,459, which was filed on Sep. 23, 2020, each of which is incorporated by reference herein in its entirety.

BACKGROUND

Intraoperative bleeding is a major complication of minimally invasive surgeries that negatively impacts surgical outcomes. Bleeding can be caused by accidental damage to the arteries or veins of the patient and may be related to surgical skills. Penza, V., et al, *FRONTIERS IN ROBOTICS AND AI,* 2017, 4: p. 15. Other causes of bleeding include anatomical anomalies or disorders, recent intake of drugs, or hemostasis disorders (which may be either congenital or acquired). Curnow, J., et al, *THE SURGERY JOURNAL,* 2016, 2(01): p. e29-e43.

If a surgeon does not detect and address bleeding complications quickly, these complications may result in the death of the patient. Intraoperative bleeding is a major cause of death during the surgical process. Philips, P. A, et al., *JOURNAL OF THE AMERICAN COLLEGE OF SURGEONS,* 2001, 192(4): p. 525-536. According to the 2004 Nationwide Inpatient Sample database, 2.23 million (or 5.8%) patients in the United States required transfusions to address complications related to bleeding. Morton, J., et al., *AMERICAN JOURNAL OF MEDICAL QUALITY,* 2010, 25(4): p. 289-296. On average, patients receiving transfusions as a result of bleeding complications were 1.7 times more likely to die, 1.9 times more likely to develop an infection, stayed in the hospital 2.5 times longer, and had treatment costs that were $17,194 higher than their counterparts with no bleeding complications.

Intraoperative bleeding is a critical and difficult problem to manage during various types of surgical procedures. Controlling patient bleeding during procedures that are already complex can be challenging for surgeons. Bleeding is of particular significance in robotic-assisted surgery. The overall complication rate of robotic-assisted surgery ranges from 4.3% to 12.0%. Patel, V. R., et al., *JOURNAL OF ENDOUROLOGY,* 2008, 22(10): p. 2299-2306; Jeong, J., et al., *JOURNAL OF ENDOUROLOGY,* 2010, 24(9): p. 1457-1461; Lebeau, T., et al., *SURGICAL ENDOSCOPY,* 2011, 25(2): p. 536-542. Bleeding is difficult to manage in minimally invasive (either robotic or traditional laparoscopic) surgery, where the surgeon completes the procedure using a remote camera view. In these cases, a small bleed can quickly lead to visual occlusion of part or the entire camera view. To effectively address bleeding, the surgeon continually monitors the camera view for bleeding to rapidly estimate the source. This estimation is particularly difficult because the source of bleeding is often submerged in, or otherwise occluded in, a pool of blood (or can quickly become submerged). Traditionally, the choices for the surgeon are limited. In cases wherein the surgeon proceeds proceed blindly, the surgeon can potentially cause more damage. Strategies to clear blood from the camera view, such as using suction to clear blood, may cause more bleeding from torn vessels and other damage. If the camera must be removed from the patient cavity for cleaning, this results in a loss of position and orientation relative to the bleed and may cause additional delays.

In addition to the risks of bleeding to patients, bleeding complications cause other problems. Hospitals and insurance providers must bear the costs associated with the numerous problems that arise as a result of surgical bleeding. For example, it is necessary to purchase tools used for the management of bleeding, pay the staff required to treat the affected patients, and manage the recovery rooms that these patients must occupy for prolonged periods following surgery due to complications from intraoperative bleeding. Hospitals have a tremendous need to minimize the resources spent on the management of intraoperative bleeding. The detection and localization of bleeding during surgery, particularly in the case of arterial bleeding, have the potential to reduce intraoperative complexity and patient blood loss.

Schafer et al. conducted a research study on intraoperative bleeding complications during robotic surgery. Schäfer, M., et al., *THE AMERICAN JOURNAL OF SURGERY,* 2000, 180(1): p. 73-77. The authors concluded that, in all, 331 (2.3%) of 14,391 patients had intraoperative bleeding complications. Moreover, 44 patients (13.3%) suffered from external bleeding of the abdominal wall, whereas the remaining 287 patients (86.7%) suffered from internal bleeding. It was noted that 33 patients (10.0%) with internal bleeding received blood transfusions, and the patients had a mean blood loss of 1,630 milliliters. Surgical hemostasis was performed in 68.0% of external bleeds and 91.0% of internal bleeds. There were 250 patients (1.8%) with post-operative bleeding complications. External bleeding occurred in 143 patients, and 107 patients developed internal bleeding. Special treatment was used in 92.0% of the cases of external bleeding. Further surgical intervention was required in half of the cases of internal bleeding. Major vascular injuries occurred in 12 patients (0.1%), with open treatment being necessary in all cases reviewed. Bleeding complications are common during laparoscopic surgery. In order to effectively manage bleeding complications, meticulous dissection techniques, immediate recognition of bleeding region, and adequate surgical treatment can help manage bleeding complications, Tensions exerted on the tissues of the patient, the unprepared cutting of arterial vessels, and accidental movements made by the surgeon are three sources of sudden bleeding during robotic and laparoscopic surgeries, which are related to the lack of experience of the surgeon. Shafaat et al. considered arterial bleeding to be one of the most significant complications that can occur during robotic surgery, requiring immediate compression or clamping to remedy the blood flow. Talab*, S. S., et al., *THE JOURNAL OF UROLOGY,* 2019, 201 (Supplement 4): p. e851-e851. The fear of bleeding is one of the factors that discourages surgeons from undertaking a minimally invasive approach. Novellis, P., et al., *ANNALS OF CARDIOTHORACIC SURGERY,* 2019, 8(2): p. 292. Hemorrhaging is the second most common complication in laparoscopic surgery, with incidents occurring in 0.2% to 1.1% of laparoscopic surgeries. Castillo, O. A., et al., *SURGICAL LAPAROSCOPY ENDOSCOPY & PERCUTANEOUS TECHNIQUES,* 2008, 18 (3): p. 315-318. This represents a challenging and/or intimidating situation for any laparoscopic surgeon. Barros, M. B., et al., *SAO PAULO MEDICAL JOURNAL,* 2005, 123(1): p. 38-41. Garisto et al. argued that strategies for managing intraoperative bleeding complications during robotic surgery could allow the safe utilization of robotic techniques in renal tumor surgery. Garisto*, J., et al., *JOURNAL OF UROLOGY,* 2019, 201 (Supplement 4): p. e848-e848. However, an important limitation of minimally invasive surgical procedures is the loss of real-time endoscopic visualization when hemorrhaging is inadvertently caused (also known as the "red-out" situation), such as in cases where bleeding occurs following obtaining a tumor biopsy sample. Ishihara, R., et al., *GASTROINTESTINAL ENDOSCOPY,* 2008, 68(5): p. 975-981.

It has also been shown that arterial bleeding can lead to intraoperative catastrophes. In the context of this study, intraoperative catastrophes can be considered as events that require unplanned surgical procedures, such as an emergency thoracotomy. Cao, C., et al., *THE ANNALS OF THORACIC SURGERY,* 2019. For example, in a study of 1,810 patients that underwent robotic anatomical pulmonary resections, the most common catastrophic event was intraoperative hemorrhaging from the pulmonary artery. Other common catastrophic events included injury to the airway, the pulmonary vein, and the liver. Cao, et al. Management of sudden bleeding situations can save time and resources both for patients and the healthcare system. However, such management depends on early detection of bleeding, especially during robotic and laparoscopic surgery, mainly before blood obscures the surgeon's vision. This early detection can help the operational team to prevent the situation from turning into a red-out and to localize and visualize the source of bleeding in the event that a red-out occurs.

SUMMARY

An example method includes identifying a first frame depicting a surgical scene; identifying a second frame depicting the surgical scene; identifying whether the second frame depicts bleeding by analyzing the first frame and the second frame; and outputting the second frame with an augmentation indicating whether bleeding is depicted in the second frame. Accordingly, if present, the bleeding can be detected, localized, assessed, or otherwise characterized.

An example system includes at least one processor and memory storing instructions that, when executed by the at least one processor, cause the at least one processor to perform operations including identifying a first frame depicting a surgical scene; identifying a second frame depicting the surgical scene; identifying whether the second frame depicts bleeding by analyzing the first frame and the second frame; and outputting the second frame with an augmentation indicating whether bleeding is depicted in the second frame. Thus, the system can detect, localize, asses, or otherwise characterize the bleeding, if present. According to various examples, the system can indicate the bleeding or absence of bleeding to a user. In some cases, the example system is a surgical robotic system.

BRIEF DESCRIPTION OF THE DRAWINGS

FIG. 6 illustrates a process for identifying and indicating the presence of bleeding based on image entropy.

FIG. 7 illustrates a process for augmenting an image depicting bleeding.

FIG. 10B depicts an area of arterial bleeding detected in a prerecorded video.

FIG. 12 includes two images demonstrating the effect of arterial bleeding on the change in the ratio of high-entropy "red" pixels within the surgery scene at two different times.

FIG. 13 shows how the process of Example 1 can be used to contour regions with a change in local entropy and label them.

FIG. 15 includes three images comparing the change in the Fourier Transform of the surgery scene.

DETAILED DESCRIPTION

Figure 1:
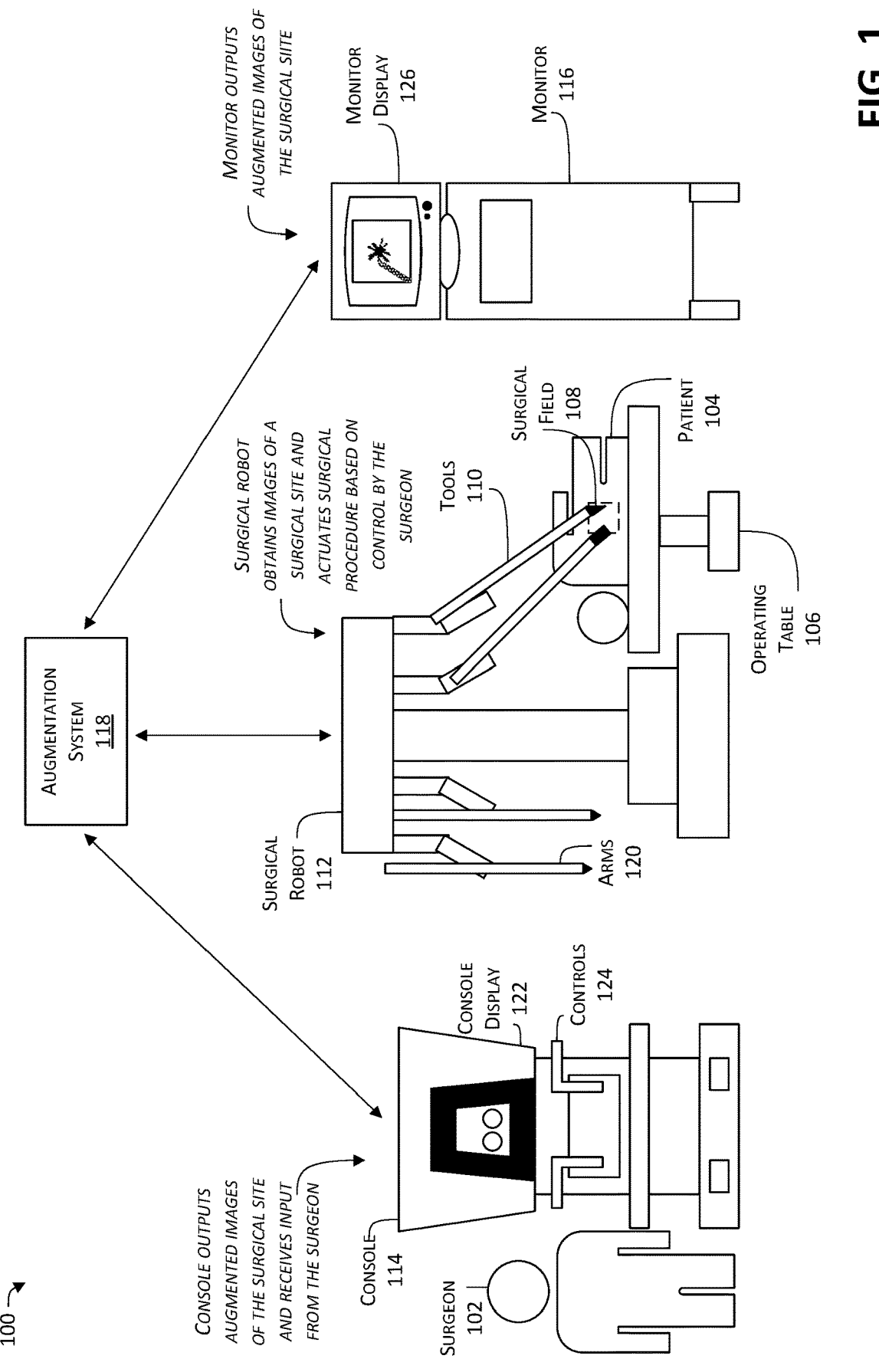
FIG. 1 illustrates an example environment for identifying intraoperative bleeding.

This disclosure describes approaches for detecting and localizing arterial bleeding, in real time, based on spatio-temporal entropy. During robotic and laparoscopic surgeries, vascular injuries may occur as a result of accidental instrument movements or cutting of the vessels, which may lead to arterial bleeding. The detection and localization of arterial bleeding during robotic or laparoscopic surgeries is critical to overcome complications associated with intraoperative hemorrhaging. If this sudden bleeding is not detected and controlled in a timely manner, it can lead to a "red-out" situation, where blood spreads throughout the surgical scene, leading to the occlusion of the surgeon's field of view. This disclosure describes vision-based techniques for monitoring abrupt changes within the surgical scene to detect arterial bleeding. Additionally, systems described herein can localize and contour the source of the bleeding. In various cases, the system computes the local entropy of the image per frame.

Various implementations described herein are distinct from other techniques for detecting bleeding within medical images. Previous methods, often performed using static images, have been developed for detecting the region of bleeding within an image and use either computer vision approaches or deep learning methods to detect bleeding spots within wireless-capsule endoscopy images. These include capsules that are swallowed and return images (wirelessly) of the inside of the body cavities as they make their way through the body.

A classification system proposed by Schafer et al. allows for the identification of bleeding complications during laparoscopy as either intraoperative or postoperative complications. Intraoperative bleeding complications refer to local hemorrhaging that occurs in the peritoneal cavity, retroperitoneum, or abdominal wall. Meanwhile, postoperative bleeding complications occur within 24 hours of surgery. Intraoperative complications are divided further into four main classes: liver bed bleeding, vascular injury, slippage of clips of the cystic artery, and miscellaneous. Kaushik, R., *JOURNAL OF MINIMAL ACCESS SURGERY,* 2010. 6(3): p. 59. Severe intraoperative bleeding is often caused by injuries to major blood vessels. The main causes of intraoperative bleeding include: (1) inadequate knowledge of the anatomical courses of the vessels under a laparoscope; (2) poor identification of anatomic layers; (3) lack of correct and effective traction and effective exposure of visual field; and (4) lack of cooperation among skillful team members. Zhang, L., et al., *ANNALS OF LAPAROSCOPIC AND ENDOSCOPIC SURGERY,* 2016. 1(7).

Mackiewicz et al. used a color histogram to extract the bleeding characteristics and a support vector machine classification to recognize bleeding within wireless capsule endoscopy images. Mackiewicz, M. W., et al., *Bleeding detection in wireless capsule endoscopy using adaptive colour histogram model and support vector classification in Medical Imaging* 2008: Image Processing. 2008. International Society for Optics and Photonics. Bourbakis et al. used neural networks to identify bleeding regions in wireless-capsule endoscopy images. Bourbakis, N., et al. A neural network-based detection of bleeding in sequences of WCE images in *FIFTH IEEE SYMPOSIUM ON BIOIN-FORMATICS AND BIOENGINEERING* (BIBE'05). 2005. IEEE. However, the neural network structure was not presented. Moreover, only 13 images were used to train the neural network, and only three images were used to test the method. In addition, the sensitivity of the method was found to be lower than 80.0% within the experiment.

Li and Meng presented a three-layer multilayer perceptron neural network to detect bleeding regions in wireless capsule endoscopy images. Li, B., et al., 2008 *CANADIAN CONFERENCE ON ELECTRICAL AND COMPUTER ENGINEERING.* 2008. IEEE. The multilayer perceptron evolved from the linear perceptron, which often has poor robustness and suffers from a lack of interference. As a result, it is seldom used in nonlinear pattern recognition. This method was measured as being 90.0% sensitive (the specificity was not presented). Pan et al. developed a neural network to detect bleeding. Pan, G., et al., *JOURNAL OF MEDICAL ENGINEERING & TECHNOLOGY,* 2009. 33(7): p. 575-581. However, it is a slow and time-consuming process to train neural networks on images, especially when handling a large amount of wireless capsule endoscopy images.

A number of pixel-based detection methods for bleeding have been proposed. Pan et al. proposed a probabilistic neural network for detecting bleeding pixels. Pan, G., et al., *JOURNAL OF MEDICAL SYSTEMS,* 2011, 35(6): p. 1477-1484. Al-Rahayfeh and Abuzneid distinguished bleeding and nonbleeding pixels via thresholding in RGB and HSV color spaces. Al-Rahayfeh, A. A. et al., arXiv preprint arXiv: 1005.5439, 2010. Hwang et al. used an expectation maximization method and R, G, and B color features to produce maximum likelihood estimates. Hwang, S., et al. *MEDICAL IMAGING* 2006: *IMAGE PROCESSING.* 2006. Other similar methods can be found in. Penna, B., et al. 2009 17TH *EUROPEAN SIGNAL PROCESSING CONFERENCE.* 2009. IEEE; Jung, Y. S., et al. 2008 *INTERNATIONAL CONFERENCE ON BIOMEDICAL ENGINEERING AND INFORMATICS.* 2008. IEEE; Lau, P. Y. et al., 2007 29TH

*ANNUAL INTERNATIONAL CONFERENCE OF THE IEEE ENGINEERING IN MEDICINE AND BIOLOGY SOCIETY.* 2007. IEEE. Since the intensity of bleeding and nonbleeding pixels often overlaps in the color channels, thresholding methods may be unreliable. Other classification methods at the pixel level usually work better but suffer from high computational costs. J. Liu et al. used the ratio of red intensity to green intensity as a feature of pixels to determine whether or not the area of interest was a bleeding spot. Liu, J. et al., *OPTIMIZATION AND ENGINEERING,* 2009. 10(2): p. 289-299. Boulougoura et al. proposed that bleeding regions could be detected using 54 statistical features (e.g., skew, standard deviation, and variance) calculated from a color histogram of six color components, such as R, G, B, H, S, and V. Boulougoura, M., et al. *SECOND INTERNATIONAL CONFERENCE ON BIOMEDICAL ENGINEERING.* 2004. Acta Press. However, while image-based methods are fast, the performance is frequently poor.

Li and Meng sought to achieve a tradeoff between accuracy and speed, leading them to propose a patch-based method based on chrominance moments combined with local binary pattern texture features. Li, B., et al., *IEEE TRANSACTIONS ON BIOMEDICAL ENGINEERING,* 2009. 56 (4): p. 1032-1039. Each wireless capsule endoscopy image was divided into 64 patches, and the 36 most informative patches were classified using a multilayer perceptron neural network. This method demonstrated high sensitivity but low specificity and accuracy. Moreover, the size, shape, and location of each bleeding region varied significantly. While the method allows the division of each image into uniform blocks, it cannot mitigate boundary patches. The multilayer perceptron evolved from the linear perceptron and is unsuitable for nonlinear pattern recognition problems.

Fu et al. attempted to address this issue by grouping pixels using super-pixel segmentation. Fu, Y., et al., IEEE *JOURNAL OF BIOMEDICAL AND HEALTH INFORMATICS,* 2013. 18(2): p. 636-642. An RGB space is used to extract features of all super-pixels, which are then fed into a vector classification machine to be classified. The edge pixels' influences are also removed using this method. Currently, there are no known algorithms that can be used to help detect arterial bleeding and localize the bleeding source in real time.

The use of entropy-based methods has not been utilized to detect bleeding during laparoscopic and robotic surgery. For example, Skilling and Bryan used an entropy approach on astronomic data. Skilling, J., et al., *MONTHLY NOTICES OF THE ROYAL ASTRONOMICAL SOCIETY,* 1984. 211: p. 111. Moreover, German et al. used entropy analysis for high dynamic range image processing. German, A., et al., *the 2ND CANADIAN CONFERENCE ON COMPUTER AND ROBOT VISION* (CRV'05). 2005. IEEE. Yan et al. used entropy calculations for gray-scale image clarification, which is required in the field of medical imagery. Yan, C., et al., *PATTERN RECOGNITION LETTERS,* 2003. 24(16): p. 2935-2941. Recently, Zong et al. proposed automatic ultrasound image segmentation based on local entropy. Zong, J.-j., et al., *COMPUTERS & MATHEMATICS WITH APPLICATIONS,* 2019. Khosravi et al. employed entropy-based textured map extraction as a tool for image segmentation. Khosravi, M., *JOURNAL OF AI AND DATA MINING,* 2019. 7(1): p. 27-34. Yue Wu et al. proposed a new image randomness measure using Shannon entropy over local image blocks. Wu, Y., et al., *INFORMATION SCIENCES,* 2013. 222: p. 323-342. Michalak proposed an approach to improve image binarization based on local entropy. Michalak, H. et al., *ENTROPY,* 2019. 21 (6): p. 562. Fang et al. suggested a hybrid active contour model based on global and local entropy for medical image segmentation. Fang, L., et al., *MULTIDIMENSIONAL SYSTEMS AND SIGNAL PROCESSING,* 2019. 30(2): p. 689-703. Dabass et al. used an entropy- and CLAHE-based intuitionistic fuzzy method for mammogram image enhancement. Dabass, J., et al., in 2019 6TH *INTERNATIONAL CONFERENCE ON SIGNAL PROCESSING AND INTEGRATED NETWORKS* (SPIN), 2019.

In various implementations described herein, the measurement of the local information encoded in each video frame of a video can be used to compute spatial and temporal entropy, which in turn can be used for localization and visualization of the bleeding. Example systems detect bleeding (e.g., stochastic bleeding, such as arterial bleeding) based on the change in entropy of surgical scenes and show the results of our algorithm on ten recorded videos from real surgeries. Specific examples of techniques used to enhance bleeding detection are described in Example 1. Example 2 reports the accuracy and robustness of an example technique for detecting bleeding from videos. This disclosure provides accurate and robust intelligent systems that assist and aid surgeons during minimally invasive surgery to prevent and control bleeding situations through the fast detection and localization of arterial bleeding. Thus, these techniques can be used as a tool for managing a red-out situation faster and with minimal damage to the patient.

Various implementations of the present disclosure automatically detect bleeding in a surgical field. Further, various implementations notify a surgeon of bleeding within the surgical field. Accordingly, the surgeon may efficiently address intraoperative bleeding, even in red out situations. In various examples, a surgical device provides information about the source, location, and magnitude of a surgical injury causing bleeding. Thus, the device can enable surgeons to address the surgical injury effectively without converting to an open procedure. In some cases in which a red out is depicted in a view of the surgical field, the device can further overlay anatomical structures within the view, so that the surgeon can rely on those anatomical structures to address the source of the bleeding.

In various examples, physiological structures in the view of the surgical field are correlated with physiological structures depicted in pre-operative images and/or other intraoperative images. Once bleeding is detected in the view of the surgical field, the correlations with the other images can be used to identify a vessel and/or structure that is the source of the bleeding. In addition, visual anatomical landmarks from the view of the surgical field can also be used to better localize and give critical information about the bleeding source. Hence, after a bleed location is determined, additional information about the nature, severity and structures involved can be provided to the surgeon.

Various implementations described herein provide improvements to the technical field of surgical technology. For instance, implementations described herein can automatically and accurately identify a source of bleeding within an intraoperative environment, and in some cases, can do so faster and more accurately than a surgeon. Furthermore, various implementations described herein can enable a surgeon to address intraoperative bleeding efficiently and effectively by providing the surgeon with augmentations that identify the bleeding and/or provide details that inform the surgeon of the surgical scene that would otherwise be obscured by the bleeding.

Implementations of the present disclosure will now be described with reference to the accompanying figures.

FIG. 1 illustrates an example environment 100 for identifying intraoperative bleeding. As illustrated, a surgeon 102 is operating on a patient 104 within the environment 100. In various cases, the patient 104 is disposed on an operating table 106.

The surgeon 102 operates within a surgical field 108 of the patient 104. The surgical field 108 includes a region within the body of the patient 104. In various cases, the surgeon 102 operates laparoscopically on the patient 104 using one or more tools 110. As used herein, the term "laparoscopic," and its equivalents, can refer to any type of procedure wherein a scope (e.g., a camera) is inserted through an incision in the skin of the patient. The tools 110 include a scope, according to particular examples. In various cases, the tools 110 include another surgical instrument, such as scissors, dissectors, hooks, and the like, that is further inserted through the incision. In various examples, the tools 110 include one or more sensors (e.g., accelerometers, thermometers, motion sensors, or the like) that facilitate movement of the tools 110 throughout the surgical field 108. In some implementations, the tools 110 include at least one camera and/or a 3-dimensional (3D) scanner (e.g., a contact scanner, a laser scanner, or the like) that can be used to identify the 3D positions of objects and/or structures within the surgical field 108. For example, images generated by the camera and/or volumetric data generated by the 3D scanner can be used to perform visual simultaneous localization and mapping (VSLAM) of the surgical field 108.

The surgeon 102 uses the view provided by the scope to perform a surgical procedure with the surgical instrument on an internal structure within the surgical field 108 of the patient 104, without necessarily having a direct view of the surgical instrument. For example, the surgeon 102 uses the tools 110 to perform an appendectomy on the patient 104 through a small incision in the skin of the patient 104.

According to various implementations, the surgeon 102 carries out the procedure using a surgical system that includes a surgical robot 112, a console 114, a monitor 116, and an augmentation system 118. The surgical robot 112, the console 114, the monitor 116, and the augmentation system 118 are in communication with each other. For instance, the surgical robot 112, the console 114, the monitor 116, and the augmentation system 118 exchange data via one or more wireless (e.g., Bluetooth, WiFi, UWB, IEEE, 3GPP, or the like) interfaces and/or one or more wired (e.g., electrical, optical, or the like) interfaces.

In various examples, the surgical robot 112 may include the tools 110. The tools 110 are mounted on robotic arms 120. For instance, a first arm is attached to a scope among the tools 110, a second arm is attached to another surgical instrument, and so on. By manipulating the movement and location of the tools 110 using the arms 120, the surgical robot 112 is configured to actuate a surgical procedure on the patient 104.

The console 114 is configured to output images of the surgical field 108 to the surgeon 102. The console 114 is includes a console display 122 that is configured to output images (e.g., in the form of video) of the surgical field 108 that are based on image data captured by the scope within the surgical field 108. In various examples, the console display 122 is a 3D display including at least two screens viewed by respective eyes of the surgeon 102. In some cases, the console display 122 is a two-dimensional (2D) display that is viewed by the surgeon 102.

The console 114 is further configured to control the surgical robot 112 in accordance with user input from the surgeon 102. The console 114 includes controls 124 that generate input data in response to physical manipulation by the surgeon 102. The controls 124 include one or more arms that are configured to be grasped and moved by the surgeon 102. The controls 124 also include, in some cases, one or more pedals that can be physically manipulated by feet of the surgeon 102, who may be sitting during the surgery. In various cases, the controls 124 can include any input device known in the art.

The monitor 116 is configured to output images of the surgical field 108 to the surgeon 102 and/or other individuals in the environment 100. The monitor 116 includes a monitor display 126 that displays images of the surgical field 108. In various examples, the monitor 116 is viewed by the surgeon 102 as well as others (e.g., other physicians, nurses, physician assistants, and the like) within the environment 100. The monitor display 126 includes, for instance, a 2D display screen. In some cases, the monitor 116 includes further output devices configured to output health-relevant information of the patient 104. For example, the monitor 116 outputs a blood pressure of the patient 104, a pulse rate of the patient 104, a pulse oximetry reading of the patient 104, a respiration rate of the patient 104, or a combination thereof.

In various implementations of the present disclosure, the augmentation system 118 is configured to identify a bleed in the surgical field 108, identify a magnitude of the bleed, identify a location of the bleed, cause details about the bleed to be indicated to the surgeon 102, or a combination thereof. In various examples, the augmentation system 118 is embodied in one or more computing systems. In some cases, the augmentation system 118 is located in the operating room with the surgical robot 112, the console 114, and the monitor 116. In some implementations, the augmentation system 118 is located remotely from the operating room. According to some examples, the augmentation system 118 is embodied in at least one of the surgical robot 112, the console 114, or the monitor 116. In certain instances, the augmentation system 118 is embodied in at least one computing system that is separated, but in communication with, at least one of the surgical robot 112, the console 114, or the monitor 116.

The augmentation system 118 receives image data from the surgical robot 112. The image data is obtained, for instance, by a scope among the tools 110. The image data includes multiple frames depicting the surgical field 108. As used herein, the terms "image," "frame," and their equivalents, can refer to an array of discrete pixels. Each pixel, for instance, represents a discrete area (or, in the case of a 3D image, a volume) of an image. Each pixel includes, in various cases, a value including one or more numbers indicating a color saturation and/or grayscale level of the discrete area or volume. In some cases, an image may be represented by multiple color channels (e.g., an RGB image with three color channels), wherein each pixel is defined according to multiple numbers respectively corresponding to the multiple color channels. In some implementations, the augmentation system 118 performs a VSLAM analysis on data obtained from the camera (mono or stereo) and/or 3D scanner among the tools 110, which enables the augmentation system 118 to maintain a 2D and/or 3D model of the surgical field 108. In some cases, another form of SLAM analysis can operate on the data obtained from the 3D scanner to generate a 3D model of the surgical field 108.

The augmentation system 118 determines whether a frame depicts a bleed in the surgical field by analyzing multiple frames in the image data. In some cases, the augmentation system 118 compares first and second frames in the image data. The first and second frames may be consecutive frames within the image data, or nonconsecutive frames. In some cases in which the first and second frames are nonconsecutive, and the augmentation system 118 repeatedly assesses the presence of bleeding on multiple sets of first and second frames in the image data, the overall processing load on the augmentation system 118 may be less than if the sets of first and second frames are each consecutive. In some implementations, the augmentation system 118 filters or otherwise processes the first and second frames in the image data.

According to particular implementations, the augmentation system 118 applies an entropy kernel (also referred to as an "entropy filter") to the first frame and to the second frame. By applying the entropy kernel, the local entropy of each pixel within each frame can be identified with respect to a local detection window. In some implementations, an example pixel in the first frame or the second frame is determined to be a "low entropy pixel" if the entropy of that pixel with respect to its local detection window is under a first threshold. In some cases, an example pixel in the first frame or the second frame is determined to be a "high entropy pixel" if the entropy of that pixel with respect to its local detection window is greater than or equal to the first threshold. According to various implementations of the present disclosure, each pixel in the first frame and each pixel in the second frame is categorized as a high entropy pixel or a low entropy pixel. Low entropy pixels are associated with homogeneity in their respective frames. One example source of homogeneity is bleeding within the surgical field 108.

The augmentation system 118 generates a first entropy map based on the first frame and a second entropy map based on the second frame. The first entropy map is a grayscale image with the same spatial dimensions as the first frame, wherein each pixel in the first entropy map respectively corresponds to the entropy level of a corresponding pixel in the first frame. For instance, an example pixel in the first entropy map will have a low value (e.g., near 0, near back, or the like) if the corresponding pixel in the first frame has a low amount of entropy, or it will have a high value (e.g., near 255, near white, or the like) if the corresponding pixel in the first frame has a high amount of entropy. Similarly, the second entropy map is a grayscale image with the same spatial dimensions as the second frame, wherein each pixel in the second entropy map respectively corresponds to the entropy level of a corresponding pixel in the second frame. Although, in some implementations, the augmentation system 118 generates entropy maps of additional frames within a video of the surgical field 108, for ease of explanation, only two frames will be described with reference to FIG. 1.

The augmentation system 118 generates a first mask based on the first entropy map and a second mask based on the second entropy map. The first mask is a binary image with the same spatial dimensions as the first frame and first entropy map, wherein each pixel in the first mask respectively corresponds to the categorization of a corresponding pixel in the first frame as a high-entropy or low-entropy pixel. For instance, an example pixel in the first mask has a first value (e.g., white, 1, or the like) if the corresponding pixel in the first frame is a low-entropy pixel (e.g., the entropy is less than a threshold) or has a second value (e.g., black, 0, or the like) if the corresponding pixel in the first frame is a high-entropy pixel (e.g., the entropy of the pixel is greater than or equal to a threshold), or vice versa. The Otsu thresholding method is one example in which the entropy maps are binarized to create the masks. See, e.g., Otsu N, *IEEE TRANSACTIONS ON SYSTEMS, MAN, AND CYBERNETICS,* 1979; 9(1): 62-66. Similarly, the second mask is a binary image with the same spatial dimensions as the second frame and second entropy map, wherein each pixel in the second mask respectively corresponds to the categorization of a corresponding pixel in the second frame as a high-entropy pixel (e.g., the local entropy of the pixel is greater than or equal to a threshold) or a low-entropy pixel (e.g., the local entropy of the pixel is less than the threshold). Although, in some implementations, the augmentation system 118 generates masks of additional frames within a video of the surgical field 108, for ease of explanation, only two frames will be described with reference to FIG. 1.

In various implementations, at least some of the low-entropy pixels in a frame correspond to regions of blood. Regions of the frame depicting blood are assumed to be relatively homogenous, with little texture. In contrast, at least some of the high-entropy pixels in the frame correspond to other structures (e.g., physiological structures) with significant texture and heterogeneity. Thus, blood can be detected by the augmentation system 118 based on the low-entropy pixels.

The augmentation system 118 determines a change in entropy between the first frame and the second frame based on the first mask and the second mask, according to some implementations. In particular examples, the augmentation system 118 generates a first masked image based on the first mask and the first frame, as well as a second masked image based on the second mask and the second frame. The first masked image is generated, in some cases, by performing pixel-by-pixel multiplication of the first mask (wherein the low-entropy pixels have values of "1" and the high-entropy pixels have values of "0," for instance) and at least one color channel (e.g., the red color channel) of the first frame. Thus, relatively high-entropy pixels in the first frame are omitted from the first masked image, but relatively low-entropy pixels in the first frame are included in the first masked image. The second masked image is generated similarly to the first masked image, but based on the second mask and the second frame.

The augmentation system 118 identifies a first pixel ratio (also referred to as an "entropy ratio") corresponding to the number of pixels in the first masked image having values greater than a particular threshold over the total number of pixels in the first masked image, and a second pixel ratio corresponding to the number of pixels in the second masked image having values greater than the particular threshold over the total number of pixels in the first masked image. In some cases, the first pixel ratio corresponds to the number of low-entropy red pixels in the first frame, and the second pixel ratio corresponds to the number of low-entropy red pixels in the second frame, wherein a "red pixel" corresponds to a pixel whose red channel exceeds a threshold. In some cases, a red pixel is a pixel whose other color channel values (e.g., green and blue channel values) are below respective thresholds. These low-entropy red pixels are assumed to correspond to bleeding within the scene depicted by the first frame and the second frame. Thus, a significant change in the number of low-entropy red pixels indicates the presence of bleeding in the second frame. According to some implementations, the total number of low-entropy red pixels are used instead of the ratio of low-entropy red pixels within each masked image. Low-entropy red pixels may also be referred to herein as "blood pixels."

The augmentation system 118 compares the first pixel ratio and the second pixel ratio. If the difference between the first pixel ratio and the second pixel ratio is less than a second threshold (e.g., 30%), then the augmentation system 118 concludes that no bleeding has been initiated or is present in the surgical field 108 depicted in the second frame. However, if the difference between the first pixel ratio and the second pixel ratio is greater than or equal to the second threshold, then the augmentation system 118 identifies bleeding in the surgical field 108 depicted in the second frame.

Upon identifying bleeding in the surgical field 108, in some cases, the augmentation system 118 further analyzes the first frame, the second frame, the first entropy map, the second entropy map, the first masked image, and/or the second masked image to identify a location and/or magnitude of the bleeding. For example, the augmentation system 118 identifies a first region of the first masked image and a second region of the second masked image with the same relative position and size, wherein the ratio of low-entropy red pixels in the second region is greater than the ratio of low-entropy red pixels in the first region by a third threshold (e.g., 50%). The first region and the second region may be smaller than the first masked image and the second masked image. For instance, the first region may be no more than a quarter of the size of the first masked image. Based on the discrepancy between the first and second regions, the augmentation system 118 may determine that a relative location of the first and second regions in the first and second masked images corresponds to a location of the bleeding in the second frame. In some examples, the augmentation system 118 determines a magnitude of the bleeding (e.g., a flow rate, a velocity, a volume, or the like) based on the magnitude of the difference between the first and second regions.

In some cases, a bleed in the surgical field 108 can be identified using other techniques. For example, the augmentation system 118 may train a machine learning model to detect bleeding and/or maintain the trained machine learning model. The machine learning model, for example, may include at least one deep learning network, such as a convolutional neural network (CNN). Videos of previous surgeries, as well as indications of when and where bleeding occurs in those videos, can be used to train the machine learning model. Once trained, the machine learning model can review video of the surgical field 108 and identify the presence of bleeding based on the video from the video of the surgical field. Machine learning-based techniques can be used as an alternative, or in addition to, entropy-based image processing techniques for detecting bleeding.

In particular examples, a combination of techniques (machine learning and image processing) are combined to detect bleeding. For instance, a multi-layer CNN is used. In the first layers of the CNN, the system convolves the image using a convolutional kernel. This is akin to processing the image for features (determined by the kernel) for example edges. The next step can be pooling, which is a step which reduces the dimensionality of the data by combining multiple neurons from one layer to another. Image processing techniques using gradient computations between frames may also be used to detect, localize, and determine the severity of the bleeding. These techniques can be used to identify the speed, accuracy, and severity of bleeds that can be detected as compared to expert surgeons analyzing the frames. In some cases, the results of the machine learning and image processing model are compared with data that was used for the training and new video data that the model was not trained with. Using this iterative process, and the accuracy algorithm will be improved until set criteria have been met.

Although in various examples described herein, the augmentation system 118 assumes that the scope among the tools 110 is not itself moving more than a threshold amount, this assumption is not required in some implementations.

In various implementations, the augmentation system 118 can cause the presence, location, and/or magnitude of the bleeding to be indicated to the surgeon 102 and/or other personnel within the environment 100. The augmentation system 118 causes the console display 122 and/or the monitor display 126 to output the second frame. If the augmentation system 118 identifies bleeding in the second frame, then the augmentation system 118 also causes the console 114 and/or the monitor 116 to output at least one augmentation indicating the presence, location, and/or magnitude of the bleeding.

In some examples, the augmentation includes a visual augmentation. For instance, the augmentation system 118 causes the console display 122 and/or the monitor display 126 to output the second frame and a visual overlay that indicates the presence, location, and/or magnitude of the bleeding. In particular examples, the visual overlay is a shape with a size and/or color that indicates the magnitude of the bleeding. In some cases, the visual overlay is located (e.g., overlaid in) in a section of the second frame that depicts the determined source of the bleeding. In some cases, the visual overlay is output in a location that is in a different portion of the second frame. In some cases, the visual overlay includes numbers and/or words indicating the presence, location, and/or magnitude of the bleeding.

According to some cases, the augmentation includes a haptic augmentation. For example, the augmentation system 118 causes the controls 124 (e.g., joysticks, handles, and/or the pedals) to vibrate based on (e.g., simultaneously as) the bleeding depicted in the second frame.

In some instances, the augmentation includes an audio augmentation. For instance, the augmentation system 118 causes at least one speaker among the console 114 or the monitor 116 to output a sound indicating the bleeding. In various implementations described herein, any output capable of indicating, to the surgeon 102, that the occurrence, the location, and/or the magnitude of bleeding can be triggered by the augmentation system 118.

In various cases, blood in the surgical field 108 obscures the source of the bleeding. This is known as a "red out" situation. In various implementations, the augmentation system 118 can further restore visibility to the source of the bleeding, even in red out situations. Thus, the augmentation system 118 further assists the surgeon 102 with addressing bleeding in the surgical field 108. For example, the augmentation system 118 can remember the locations of physiological structures in the surgical field 108 based on previous frames depicting the surgical field 108, and may augment the red out frames displayed to the user with the estimated locations of the physiological structures.

According to some examples, the augmentation system 118 identifies a region depicting blood in the second frame. In some cases, the region overlays the source of the bleeding depicted in the second frame. The augmentation system 118 identifies an equivalent region in the first frame that depicts a physiological structure (e.g., a blood vessel, an artery, organ tissue, or the like) that is obscured by the bleeding in the second frame. The augmentation system 118 generates an overlay based on the equivalent region in the first frame. The augmentation system 118 causes the console display 122 and/or the monitor display 126 to output the second frame and the overlay based on the equivalent region. Accordingly, even if the second frame depicts blood obscuring the physiological structure, the augmentation system 118 assists the surgeon 102 with estimating the location of the physiological structure with respect to the second frame. Further, in some cases, the augmentation system 118 outputs the overlay depicting the physiological structures in multiple subsequent frames depicting the surgical field 108 in which the physiological structure is obscured by blood. In some cases, the augmentation system 118 identifies the shape and position of the physiological structures by performing VSLAM on the surgical field, and outputs depictions of the estimated physiological structures as an overlay over the region of the frame that is obscured by blood.

In various implementations described herein, the augmentation system 118 indicates the presence of bleeding in the surgical field 108 to the surgeon 102 based on image data depicting views of the surgical field 108. In some examples, the augmentation system 118 further indicates the position and/or magnitude of the bleeding based on the image data. According to some cases, the augmentation system 118 also uses previous image data to depict a physiological structure that is obscured by bleeding. Thus, the augmentation system 118 assists the surgeon 102 with efficiently identifying and stopping interoperative bleeding laparoscopically.

Figure 2:
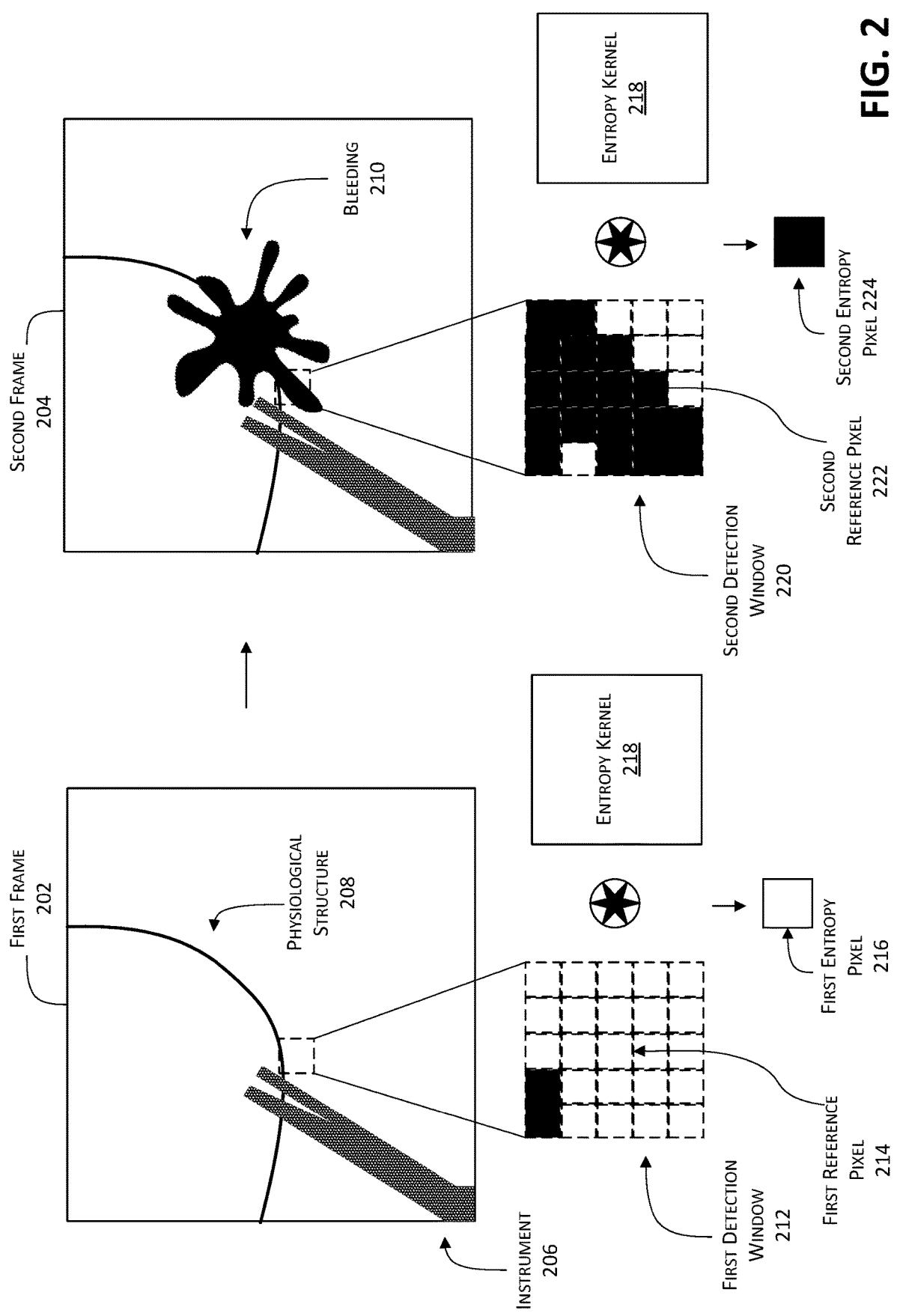
FIG. 2 illustrates example techniques for generating entropy pixels representing the entropy of pixels in frames depicting a scene of interest.

FIG. 2 illustrates example techniques for generating entropy pixels representing the entropy of pixels in frames depicting a scene of interest. In various cases, the entropy pixels are generated by an augmentation system, such as the augmentation system 118 described above with reference to FIG. 1.

In the example illustrated in FIG. 2, a first frame 202 depicts a scene of interest (e.g., the surgical field 108 described above with reference to FIG. 1) at a first time and a second frame 204 depicts the scene of interest at a second time. The second time is subsequent to the first time. In various instances, the first frame 202 and the second frame 204 are obtained with by the same imaging device, such as the same scope (e.g., a laparoscope, an endoscope, or some other camera). According to some examples, the first frame 202 and the second frame 204 are consecutive images, such that a difference between the first time and the second time is a sampling period of the imaging device. In some cases, the first frame 202 and the second frame 204 represent downsampled images, in which the difference between the first time and the second time is greater than the sampling period of the imaging device. For instance, the first frame 202 and the second frame are nonconsecutive frames in a video.

In FIG. 2, the first frame 202 and the second frame 204 are two-dimensional images, but implementations are not limited thereto. In some cases, the first frame and the second frame 204 are represented by arrays of pixels. Each pixel is defined according to an area (e.g., a square area) and at least one value. In some examples in which the first frame 202 and the second frame 204 are color images, a value of a pixel is defined according to three numbers (e.g., each being in a range of 0 to 255, inclusive) corresponding to red, green, and blue (RGB) components, or cyan, magenta, yellow (CMY) components, of the color of the area defined by the pixel. In some examples in which the first frame 202 and the second frame 204 are binary images, a value of a pixel is defined as 0 (e.g., black) or 1 (e.g., white). In some examples in which the first frame 202 and the second frame 204 are grayscale images, a value of a pixel is defined according to a single number in a range (e.g., of 0 to 255, inclusive) representing a gray value of the area defined by the pixel. However, implementations are not limited to the specific color models described herein. In some cases, the first frame 202 and the second frame 204 represent a single color channel, such as the red component of image data obtained from the imaging device.

As shown, the first frame 202 depicts an instrument 206 and a physiological structure 208 within the scene of interest. However, bleeding 210 has occurred between the first time and the second time. Thus, the second frame 204 depicts the bleeding 210. Further, the bleeding 210 depicted in the second frame 204 partially obscures the physiological structure 208.

To sense the bleeding 210, entropy maps including entropy pixels are generated based on the first frame 202 and the second frame 204. For instance, a first detection window 212 is defined as a square portion of pixels in the first frame 202. Although the first detection window 212 is depicted as having dimensions of 5×5 pixels in FIG. 2, implementations are not limited thereto. For example, the first detection window 212 can have dimensions of 9×9 pixels, 11×11 pixels, or the like. The first detection window 212 includes a first reference pixel 214. In some cases, the first reference pixel 214 is located in the center of the first detection window 212.

In various cases described herein, bleeding can be detected in a frame by measuring the uniformity of different regions of the frame. The uniformity of the different regions can be determined based on the concept on entropy. For instance, an entropy filter can be used to produce a texture distribution of a frame. A morphological methodology using the entropy filter can be used to extract salient motions or objects that appear to be moving within an entropy mapped frame. The entropy of the frame can be representative of a variational statistical measurement of the frame. The morphological methodology can have more robustness in relation to noise compared to traditional difference-based methods. See Jaiswal, *J. OF GLOBAL RESEARCH IN COMPUTER SCIENCE*, 2011, 2(6): pp. 35-38. The detection accuracy of the morphological methodology can be improved by using the entropy from multiple frames in a video.

According to various implementations, a series of processing steps can be performed in order to detect bleeding within one or more frames of a video. First, a frame depicting a surgical scene can be generated (e.g., the frame may be part of a video depicting the surgical scene) and can be converted from the RGB color model to the grayscale color model to eliminate hue and saturation components, but to retain a luminance component of the first frame. A moving, two-dimensional of k by k window (wherein k is an integer number of pixels) may be applied to the grayscale image, and the local entropy of the image in the window is computed to generate a grayscale entropy map of that frame. The entropy map can be binarized into a mask, such that pixels corresponding to lower than a threshold entropy are defined with one value (e.g., have values of "1") and the other pixels are defined with another value (e.g., have values of "0"). The mask may be multiplied by the RGB frame to produce a masked RGB frame. The total number of low-entropy pixels in the entropy map of the frame can be determined and compared to that of a previous frame. If the change is greater than a threshold (e.g., a pre-set threshold), the original frame can be labeled as "dynamic." Temporal change in the entropy maps is the base for detecting (arterial) bleeding, which is a stochastic event. An abrupt increase in the number of low-entropy pixels whose red channel component exceeds a threshold (also referred to as "red" pixels) from the first masked RGB frame to the second masked RGB frame can be correlated to regions of higher entropy in the "dynamic" image sequence. Lower entropy regions of the subsequent frame can be identified, and regions of the previous frame corresponding to the lower-entropy regions of the subsequent frame can be extracted and overlaid on the subsequent frame, thereby providing a visualization.

Local entropy can be used to quantify and represent homogeneity of a small area in a frame. More specifically, for a square region of size k by k, the local entropy can be calculated according to the following Equation 1:

$$LE(\Psi_r) = \sum_{i=0}^{k} \sum_{j=0}^{k} p_{ij} \log_2(p_{ij}) \qquad \text{Eq. 1}$$

where $p_{ij}$ represents the probability function for a pixel [i,j]. The entropy map is represented as a grayscale image with higher intensities for regions that are less homogenous (regions that correspond to areas of higher entropy and/or information) and lower intensity for the regions they are more homogenous (regions that correspond to areas of lower entropy and/or information).

Local entropy values can be used to evaluate the gray-level spread in the histogram. A local entropy of a window is associated with the variance exhibited by pixels in the window and represents textural features of the pixels in the window. Computing the local entropy of each pixel in a frame can be used to generate an entropy map of the frame. The generated entropy map can be a grayscale image which maps the different regions of the frame with different amounts of homogeneity. In the context of a frame depicting bleeding (e.g., arterial bleeding), the frame can be associated with lower local entropy values in bleeding regions than in non-bleeding regions. This is because the areas covered by blood are more homogenous (e.g., uniform) due to blood cells and the texture of bloody areas.

In some cases, bleeding can be detected in a video depicting a robotic surgery using the concept of entropy and homogeneity. In some examples, the entropy map of each frame in the video can be generated by calculating the local entropy of each pixel in each frame. The entropy maps may be represented as grayscale images. Entropy masks can be generated by binarizing the entropy maps, such that areas corresponding to relatively high entropy levels are set at a first value and areas corresponding to relatively low entropy levels are set at a second value. The frames can be masked with their respective entropy masks. The change of randomness/homogeneity in consecutive frames over time can be calculated based on the masked frames. Hence, $LE(\Psi_r)$ and $p_{ij}$ can be functions of time. For clarity, these metrics can be expressed as $LE(\Psi_{r,n})$ and $p_{ij}(n)$, respectively, where n means the n-th frame in the video.

The change in intensity due to bleeding (e.g., arterial bleeding) can be quantified through rate of local change of uniformity that is formulated in accordance with Equation 2:

$$RLE(\Psi_r) = \frac{LH(\Psi_r, n) - LH(\Psi_r, n-1)}{LH(\Psi_r, n-1)} \qquad \text{Eq. 2}$$

Where RLE is the relative local entropy of region Yr. Equation 2 can be used to quantify two characteristics of a video: the rate of change in homogeneity of frames within the video through the value of $RLE(\Psi_r)$ of coordinate ij, which can be interpreted as the spatial homogeneity within the image. This means that by setting the value of $RLE(\Psi_r)$ to be less than a certain value, thresholds of the ratio of low-entropy red pixels, it is possible to detect bleeding, and the i and j values can be used to locate and outline the region of interest, which may correspond to the origin of the bleeding.

For real-time detection of bleeding, changes in the distributions of entropy maps corresponding to consecutive frames can be tracked as the frames are obtained (e.g., in a video stream). That is, the entropy map from each frame can be compared to the entropy map of the previous frame over a time period. Each entropy map can localize regions with a high degree of homogeneity. For the sake of quantification, the entropy maps can be binarized, and the number of low-entropy pixels (e.g., the total number of pixels corresponding to less than a threshold entropy) can be calculated as an indicator of uniformity of different regions of the content of the video with respect to time.

To identify bleeding regions, an entropy map can be divided into two types of regions: homogeneous regions and heterogenous regions. The entropy map may be binarized, which can allow for the identification of uniform regions within the video frame with low intensity, which may be visualized using black pixels, and heterogenous (texturized) regions with the highest intensity, which may be visualized as white pixels. When a current RGB frame is masked by its binarized entropy map, a masked RGB frame is produced, wherein pixels corresponding to the heterogenous regions are removed and RGB pixels corresponding to the homogenous regions (which may include pixels depicting blood) are retained. The pixels corresponding to the homogenous regions are also referred to as "color" pixels. Some of the color pixels may include what are referred to herein as "red" pixels.

The red pixels within the masked RGB frame indicate the homogeneity within an image introduced by bloody pixels. Measuring the number of red pixels (e.g., pixels whose red channel value exceeds a certain threshold) in the masked frame, and the variation of the numbers of red pixels in multiple successive masked frames, allows for detection of bleeding frames as well as and localization of the bloody spots. In other words, the number and distribution of low-entropy red pixels (also referred to as blood pixels) in the original frame are indicative of bleeding depicted in the original frame.

The thresholds and rates of change of the entropy can be identified by computing the rate of change between red pixels for two consecutive masked-RGB frames. Comparing the raw temporal entropies of two successive frames may lead to high sensitivity to small changes in local uniformity, causing large fluctuation and poor robustness. Lack of robustness will, in turn, lead to false detection of bleeding. To improve robustness, a moving average low-pass filter can be applied to the masked frames to smooth the changes in entropy for one or more previous frames preceding the current frame. The threshold for detecting the arterial bleeding when computing the temporal entropy can be represented by the following Equation 3, and may be proportional to the ratio of the image size to the size of the neighborhood (k by k) that is used for generating the entropy map:

$$TE_{Th} \propto \frac{w \times h}{LE_w \times LE_h}$$

<div align="right">Eq. 3</div>

This threshold can be computed by introducing the coefficient $\alpha$, which is an empirically derived value (e.g., a constant). The following Equation 4 can be used to calculate the threshold based on $\alpha$.

$$TE_{Th} = \alpha \times \frac{w \times h}{A_L}$$

<div align="right">Eq. 4</div>

Here, w is the width of input image, h is the height of the image, and $A_L$ is the window area used for computing the local entropy. A is the empirical coefficient. For example, $\alpha$ can be empirically derived based on training video sets. Adjusting the value of a can impact the sensitivity and/or specificity of the method. Thus, the value of a can be set in order to achieve $\alpha$ particular sensitivity and/or specificity when the method is tested with respect to the training video sets. In some experimental samples, setting the value of $\alpha$ equal to 0.01 achieved acceptable results in terms of sensitivity and specificity.

As previously mentioned, the detection and localization of arterial bleeding are based on the number of low-entropy red pixels within the masked RGB frame. Setting the appropriate threshold for counting the number of low-entropy red pixels for a certain interval can play a critical role in avoiding false detection and localization of arterial bleeding. This threshold is based on the following Equation 5:

for $p \in M^{(w \times h)}$, if $(P_R) - \sigma_R < p_R < (P_R) \pm o_R$ then $p$ is *red* pixel <div align="right">Eq. 5</div> where p is any random pixel and belongs to the masked RGB frame M with a size of w×h, $(P_R)^-$ is the mean of the pixels' red channel intensities of the masked RGB frame, and $\sigma_R$ is the standard deviation. After detecting a masked frame depicting bleeding, an indication of the bleeding can be output with the frame. For example, at least a portion of the masked frame can be overlaid on the original frame to provide better visualization to the user.

Referring back to FIG. 2, a first entropy pixel 216 is generated by calculating the entropy within the first detection window 212 with respect to the first reference pixel 214. In various cases, the first entropy pixel 216 is generated by applying (e.g., convolving or cross-correlating) an entropy kernel 218 with the first detection window 212. For example, a value of the first entropy pixel 216 is based on an output of a convolution operation of a matrix representing the values of the pixels in the first detection window 212 with a matrix defining the entropy kernel 218. In some cases, the value of the first entropy pixel 216 is based on a Shannon entropy of the first detection window 212. In various cases, the value of the first entropy pixel 216 is based on a local entropy with respect to the first reference pixel 214.

In some examples, the value of the first entropy pixel 216 is binarized. For instance, if the entropy of the first detection window 212 is greater than or equal to a first threshold, then the first entropy pixel 216 is assigned a first value (e.g., 0). If the entropy of the first detection window 212 is less than the first threshold, then the first entropy pixel 216 is assigned a second value (e.g., 1). In the example illustrated in FIG. 2, the first entropy pixel 216 is assigned the first value, indicating that the first reference pixel 214 is a high-entropy pixel.

According to various implementations, a first entropy mask including multiple entropy pixels (including the first entropy pixel 216) is generated based on the first frame 202. The first entropy mask is a binary image, wherein each pixel of the first entropy mask indicates an entropy associated with a corresponding pixel in the first frame 202. The first frame 202 and the first entropy mask may have the same dimensions. In various cases, the first detection window 212 is a sliding window that can be used to generate the entropy of each pixel in the first frame 202.

Similarly, a second entropy mask is generated for the second frame 204. As illustrated in FIG. 2, a second detection window 220 (similar to the first detection window) is used to determine the entropy associated with a second reference pixel 222 in the second frame 204. A second entropy pixel 224 is generated by applying the entropy kernel 218 to the second detection window 220. A value of the second entropy pixel 224 is the binarized output of the application of the entropy kernel 218 to the second detection window 220. In the example illustrated in FIG. 2, the entropy of the second reference pixel 222 is less than the first threshold, such that the second entropy pixel 224 has the second value, thereby indicating that the second reference pixel 222 is a low-entropy pixel. In some cases, a second entropy mask representing the entropy of each pixel in the second frame 204 is generated.

The first and second entropy masks can be used to detect the bleeding 210 in the second frame 204. In various cases, an indication of the bleeding 210 can be output to a user, such as a surgeon performing a procedure depicted in the first frame 202 and the second frame 204.

Figure 3:
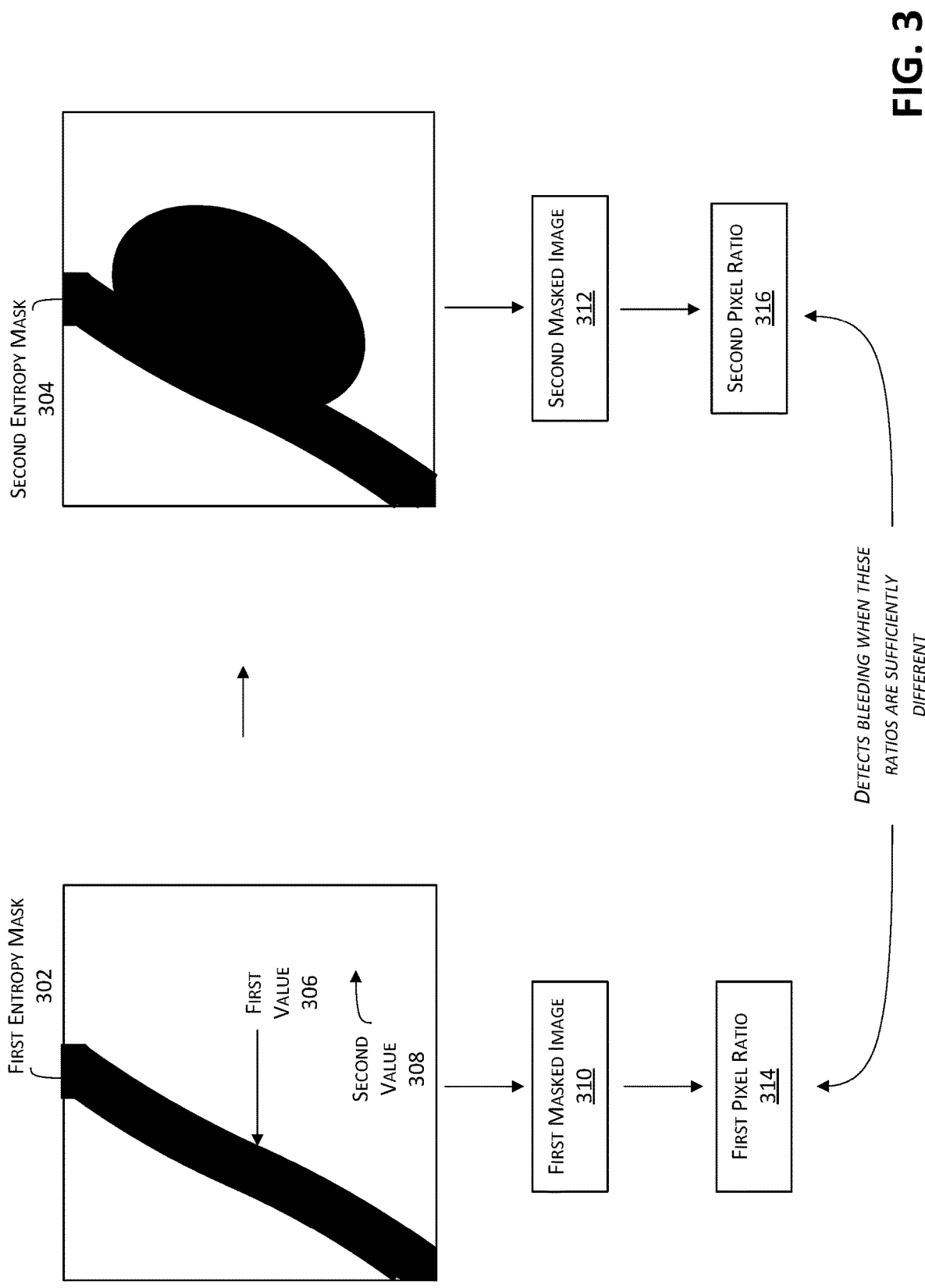
FIG. 3 illustrates an example of a technique for identifying the presence of bleeding based on entropy maps.

FIG. 3 illustrates an example of a technique for identifying the presence of bleeding based on entropy maps. Specifically, FIG. 3 illustrates a first entropy mask 302 and a second entropy mask 304. In some implementations, the first entropy mask 302 is generated based on the first frame 202 described above with reference to FIG. 2, and the second entropy mask 304 is generated based on the second frame 204 described above with reference to FIG. 2. The first entropy mask 302 is a binarized version of the first entropy map and the second entropy mask 304 is a binarized version of the second entropy map. In various cases, the first entropy mask 302 has the same pixel dimensions (e.g., number of columns and/or rows of pixels) as the first frame 202, and the second entropy mask 304 has the same pixel dimensions as the second frame 204. For example, the first entropy mask 302 includes the first entropy pixel 216 and the second entropy mask 304 includes the second entropy pixel 224. According to particular examples, the technique illustrated by FIG. 3 is performed by a system, such as the augmentation system 118 described above with reference to FIG. 1 and/or a separate computing system.

The first entropy mask 302 and the second entropy mask 304 are each binary images, according to various implementations. Some of the pixels in the first entropy mask 302 and the second entropy mask 304 have a first value 306 (e.g., 1, which is shown in FIG. 3 as black). The first value 306 indicates pixels in the first frame 202 and the second frame 204 with calculated entropy values that are less than a first threshold. The remaining pixels in the first entropy mask 302 and the second entropy mask 304 have a second value 308 (e.g., 0, which is shown in FIG. 3 as white). The second value 308 indicates pixels in the first frame 202 and the second frame 204 with calculated entropy values that are greater than or equal to the first threshold.

A first masked image 310 is generated based on the first entropy mask 302 and the first frame 202. In various examples, the first masked image 310 represents at least a subset of the pixels of the first frame 202 with entropies that are less than or equal to the first threshold. In particular implementations, the first masked image 310 represents the subset of the red channel pixels (the RGB pixels with green and/or blue channel removed) of the first frame 202 with entropies that are less than or equal to the first threshold. For instance, if the first value 306 is 1, the first masked image 310 is generated by performing pixel-by-pixel multiplication of the first entropy mask 302 and the first frame 202 (e.g., the red channel of the first frame 202). In some cases, the first masked image 310 is generated by convolving or cross-correlating the first entropy mask 302 and the first frame 202.

Similarly, a second masked image 312 is generated based on the second entropy mask 304 and the second frame 204. In various examples, the second masked image 312 represents at least a subset of the pixels of the second frame 204 with entropies that are less than or equal to the first threshold. In particular implementations, the second masked image 312 represents the subset of the red channel pixels (green and/or blue channel removed) of the second frame 304 with entropies that are less than the first threshold. For instance, if the first value 306 is 1, the second masked image 312 is generated by performing pixel-by-pixel multiplication of the second entropy mask 304 and the second frame 204 (e.g., the red channel of the second frame 204).

A first pixel ratio 314 is generated based on the first masked image 310. In various examples, the first pixel ratio 314 represents the number of red pixels in the first masked image 310 (e.g., pixels whose red channel values are greater than a particular threshold) over the total number of pixels in the first masked image 310. Thus, the first pixel ratio 314 can correspond to the ratio of low-entropy red pixels in the first frame 202.

Similarly, a second pixel ratio 316 is generated based on the second masked image 312. In various examples, the second pixel ratio 316 represents the number of red pixels in the second masked image 312 (e.g., pixels whose red channel values are greater than a particular threshold) over the total number of pixels in the second masked image 312. Thus, the second pixel ratio 316 corresponds to the ratio of low-entropy red pixels in the second frame 204.

In various implementations, the occurrence of bleeding in the second frame 204 is detected based on the first pixel ratio 314 and the second pixel ratio 316. In some implementations, the presence of bleeding is detected when the first pixel ratio 314 and the second pixel ratio 316 are sufficiently different. For instance, a difference between the first pixel ratio 314 and the second pixel ratio 316 is compared to a second threshold. In various cases, the difference relates to the change in global entropy from the first frame 202 to the second frame 204. If the difference is less than the second threshold, then bleeding is determined to not be depicted in the second frame 204. However, if the difference is greater than or equal to the second threshold, then the bleeding (e.g., the bleeding 210) is determined to be depicted in the second frame 204.

The second threshold is adjustable, in some implementations. For example, the second threshold can be set at a relatively high level (e.g., 40%) for surgical procedures that are particularly sensitive to intraoperative bleeding, such as neurological procedures. In contrast, the second threshold can be set at a relatively high level (e.g., 10%) for surgical procedures that are relatively insensitive to intraoperative bleeding, such as orthopedic procedures. In various cases, a surgeon or other user can input the sensitivity and/or the second threshold into the system (e.g., the augmentation system 118) comparing the first pixel ratio 314 and the second pixel ratio 316.

In the example illustrated in FIG. 3, the first pixel ratio 314 and the second pixel ratio 316 are sufficiently different to detect the bleeding in the second frame 204. In various cases, the system is configured to output an indication of the bleeding to the surgeon and/or any other users associated with the surgical procedure.

Figure 4:
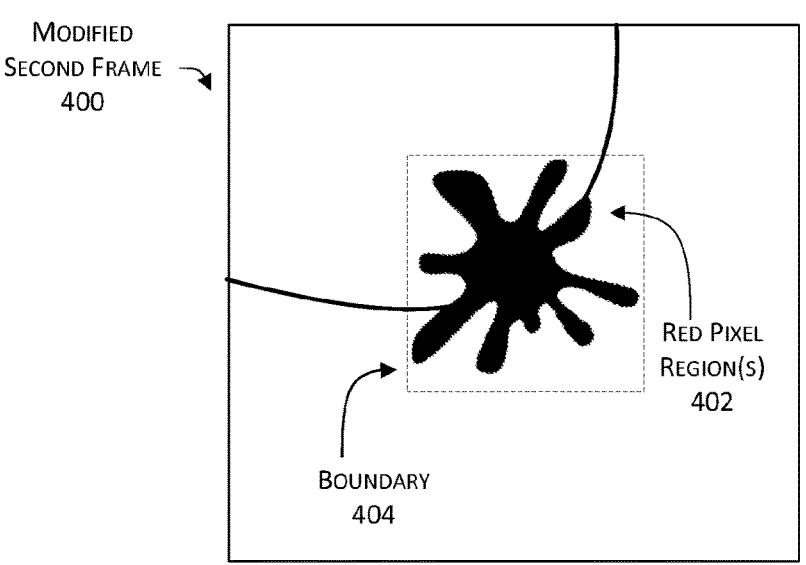
FIG. 4 illustrates a technique for locating and identifying a magnitude of bleeding in a surgical scene.

FIG. 4 illustrates a technique for locating and identifying a magnitude of bleeding in a surgical scene. For instance, the technique illustrated in FIG. 4 is applied to the second frame 204 based on the identification that the difference between the first pixel ratio 314 and the second pixel ratio 312. According to various implementations, the location and magnitude of bleeding can be determined by a system, such as the augmentation system 118 described above with reference to FIG. 1.

In various cases in which the second frame 204 includes multiple color channels, non-red color channels are removed from the second frame 204. Thus, a modified second frame 400 representing the red color channel of the second frame 204 is generated. If the second frame 204 represents the red color channel of imaging data, then the second frame 204 and the modified second frame 400 are equivalent. The red color components within the second frame 204, which are represented by the modified second frame 400, can be used to better estimate the blood within the second frame 204 than a combined image with multiple color channels. For example, by considering the red color channel rather than other color channels, bleeding can be distinguished from other homogenous subjects in the second frame 204. In some cases, the red pixels are defined according to multiple color channels. For example, an RGB pixel can be defined as a red pixel if the red channel value of the pixel is greater than a first threshold, the green channel value of the pixel is less than a second threshold, and a blue channel value of the pixel is less than a third threshold.

According to particular implementations, one or more red pixel regions 402 in the second frame 400 are identified. Further, at least one boundary 404 is generated around at least one of the identified red pixel region(s) 402. For instance, the boundary 404 is generated around the red pixel region(s) 402 that are greater than a threshold size (e.g., defined in terms of pixel height, pixel width, and/or pixel volume). Although the boundary 404 is depicted in FIG. 4 as a square, implementations are not so limited. For instance, in some cases, the boundary 404 is defined as an edge of the red pixel region(s) 402.

The location of the identified bleeding is defined, in various cases, as a location inside of the red pixel region(s) 402 and/or the boundary 404. In some cases, the centroid of the boundary 404 is identified and indicated as the source of the bleeding. Further, the magnitude of the bleeding is estimated, in some examples, based on a size of the red pixel region(s) 402 and/or the boundary 404. In various examples, the location and/or the magnitude of the bleeding is output to a surgeon and/or other user.

Figure 5A:
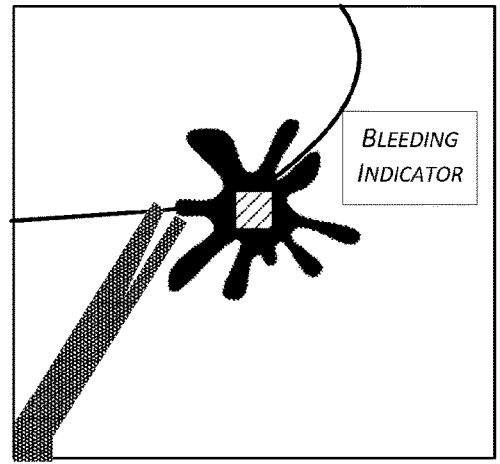
FIGS. 5A and 5B illustrate examples of augmented images indicating bleeding.
Figure 5B:
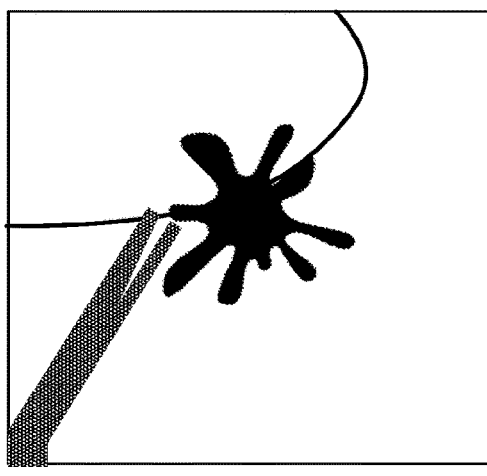

FIGS. 5A and 5B illustrate examples of augmented images indicating bleeding. In various cases, the augmented images illustrated in FIGS. 5A and 5B can be generated by a system (e.g., the augmentation system 118 described above with reference to FIG. 1).

FIG. 5A illustrates an example of an augmented frame 500 that indicates the location and magnitude of bleeding within the second frame 204. In various cases, the augmented frame 500 includes the second frame 204 as well as an overlay shape 502 and an overlay key 504. The overlay shape 502, in some examples, is output in a region of the detected bleeding in the second frame 204. According to some instances, the overlay shape 502 has a shape and/or a color that indicates the position and/or magnitude of the bleeding. In some cases, the overlay shape 502 is omitted from the augmented frame 500. The overlay key 504, in various cases, is output outside of the detected bleeding in the second frame 204. The overlay key 504 includes words, numbers, shapes, colors, and/or any other indicator of the position and/or magnitude of the bleeding. In some cases, the overlay key 504 is omitted from the augmented frame 500.

FIG. 5B illustrates another example of an augmented frame 506. The augmented frame 506 includes the second frame 204 as well as a structural augmentation 508. The structural augmentation 508 represents a physiological structure that is obscured by the bleeding in the second frame 204. In some instances, the structural augmentation 508 is derived based on a previous frame, such as the first frame 202. For example, the structural augmentation 508 includes a portion of the first frame 202 that indicates the physiological structure obscured by the bleeding. In some cases, the structural augmentation 508 is generated based on pre-operative imaging. In particular examples, the structural augmentation 508 is generated based on VSLAM (or an alternative SLAM-based) image analysis and/or volumetric data representing the physiological structure prior to the bleeding.

FIGS. 6 and 7 illustrate processes that can be performed by various devices, such as computing systems. In some cases, the processes illustrated in FIGS. 6 and 7 can be performed by a medical device, a surgical system, a surgical robot, or some other system (e.g., the augmentation system 118 described above with reference to FIG. 1). Unless otherwise specified, the steps illustrated in FIGS. 6 and 7 can be performed in different orders than those specifically illustrated.

FIG. 6 illustrates a process 600 for identifying and indicating the presence of bleeding based on image entropy. At 602, an entity performing the process 700 identifies a first frame of a surgical field. The surgical field can also be referred to as a surgical scene. In some cases, the first frame is obtained from a scope (e.g., an arthroscope). For instance, the first frame is obtained from a scope that is manipulated via a surgical robot. Bleeding is not depicted in the first frame, according to various examples. In some cases, the first frame is filtered.

At 604, the entity identifies a second frame of the surgical field. The first frame and the second frame are obtained by the same scope, in various cases. The first frame is obtained at a first time and the second frame is obtained at a second time. In various examples, the first time occurs prior to the second time. In some cases, the first frame and the second frame are downsampled frames from a video, wherein the video includes one or more additional frames obtained between the first time and the second time. In some examples, the first frame and the second frame are red channel frames of RBG images depicting the surgical scene. In some cases, the second frame is filtered.

At 606, the entity generates a first entropy map based on the first frame. The first entropy map represents local entropies of first pixels in the first frame, according to particular implementations. For instance, an entropy kernel is applied to the first frame. In some cases, the entropy kernel is convolved with a sliding detection window of the first frame. In some cases, the detection window has an area that is between 7 by 7 pixels and 15 by 15 pixels. For instance, the detection window is 9 by 9 pixels.

According to various implementations, a first entropy mask is generated based on the first entropy map. For example, the first entropy mask is generated by calculating a local entropy of a pixel in the first frame. If the local entropy does not exceed a particular threshold, then a corresponding pixel in the first entropy mask is assigned a first value (e.g., 1). If, on the other hand, the local entropy exceeds the particular threshold, then the corresponding pixel is assigned a second value (e.g., 0). In some cases, the particular threshold is set according to a user input. Each pixel in the first entropy mask is generated in accordance with this process, according to various examples. The first entropy mask is a binary image.

At 608, the entity generates a second entropy map based on the second frame. The second entropy map is generated similarly to the first entropy map, for instance. Further, a second entropy mask can be generated based on the second entropy map At 610, the entity generates pixel ratios of the first and second frames based on the first and second entropy maps. According to some cases, the pixel ratios are generated by generating first and second masked images. The first masked image, for instance, is generated by multiplying, pixel-by-pixel, the first entropy mask and the first frame. The second masked image, similarly, is generated by multiplying, pixel-by-pixel, the second entropy map and the second frame. A first pixel ratio corresponds to the number of red pixels in the first masked image. For example, the first pixel ratio corresponds to pixels with red values that exceed a particular threshold (and, in some cases, whose blue and green values are less than respective thresholds) over the total number of pixels in the first masked image. A second pixel ratio corresponds to the number of pixels in the second masked image with red values that exceed the particular threshold (and, in some cases, whose blue and green values are less than the respective thresholds) over the total number of pixels in the second masked image.

At 612, the entity determines whether a difference between the pixel ratios is greater than a threshold. In some cases, this threshold is set according to a user input. If the difference is determined to not exceed the threshold at 612, then the process proceeds to 614. At 614, the entity outputs the second frame without an augmentation. In various implementations, as long as the difference between the pixel ratios is relatively small, the entity can conclude that no bleeding is present in the second frame.

If, on the other hand, the difference is determined to exceed the threshold at 612, then the process proceeds to 616. At 616, the entity identifies bleeding depicted in the second frame. At 618, the entity outputs the second frame with an augmentation indicating the bleeding and/or a physiological structure obscured by the bleeding. For instance, the second frame is output with a visual overlay indicating the bleeding. In some cases, the second frame is output with an audio signal and/or a haptic signal indicating the bleeding. In some cases, the second frame is output with an augmentation that indicates the magnitude and/or location of the bleeding. According to some implementations, a depiction of the physiological structure is extracted from the first frame and used to augment the second frame with an indication of the physiological structure, which is otherwise obscured by the bleeding in the second frame.

FIG. 7 illustrates a process 700 for augmenting an image wherein bleeding at least partially obscures a physiological structure. At 702, an entity performing the process 700 identifies a first frame depicting a surgical scene. The surgical field can also be referred to as a surgical scene. In some cases, the first frame is obtained from a scope (e.g., an arthroscope). For instance, the first frame is obtained from a scope that is manipulated via a surgical robot. Bleeding is not depicted in the first frame, according to various examples. In some cases, the first frame is filtered.

At 704, the entity identifies a second frame depicting the surgical scene. The first frame and the second frame are obtained by the same scope, in various cases. The first frame is obtained at a first time and the second frame is obtained at a second time. In various examples, the first time occurs prior to the second time. In some cases, the first frame and the second frame are downsampled frames from a video, wherein the video includes one or more additional frames obtained between the first time and the second time. In some examples, the first frame and the second frame are RBG images depicting the surgical scene. In some cases, the second frame is filtered.

At 706, the entity identifies whether the second frame depicts bleeding by analyzing the first frame and the second frame. In various cases, the entity calculates local entropies of pixels in the first frame and the second frame. Pixels that are associated with less than a first threshold of local entropy are extracted from the first frame and the second frame. The red pixels in each frame with local entropies that are less than the first threshold are determined. The red pixels can include pixels whose red color channel values are greater than a particular threshold. In some cases, the red pixels can include pixels whose blue and green channel values are less than respective thresholds. In some cases, ratios of the low-entropy red pixels in the frames are compared. If there is a sufficient increase in the number of low-entropy red pixels from the first frame to the second frame, then the second frame is identified as depicting bleeding.

At 708, the entity outputs the second image with an augmentation indicating bleeding and/or an augmentation indicating a physiological structure obscured by the bleeding. For instance, an area of the second frame depicting the bleeding is identified. A corresponding area of the first frame is extracted. The corresponding area depicts a physiological structure that is obscured by the bleeding in the second frame. An overlay indicating the physiological structure is generated and output with the second frame.

Figure 8:
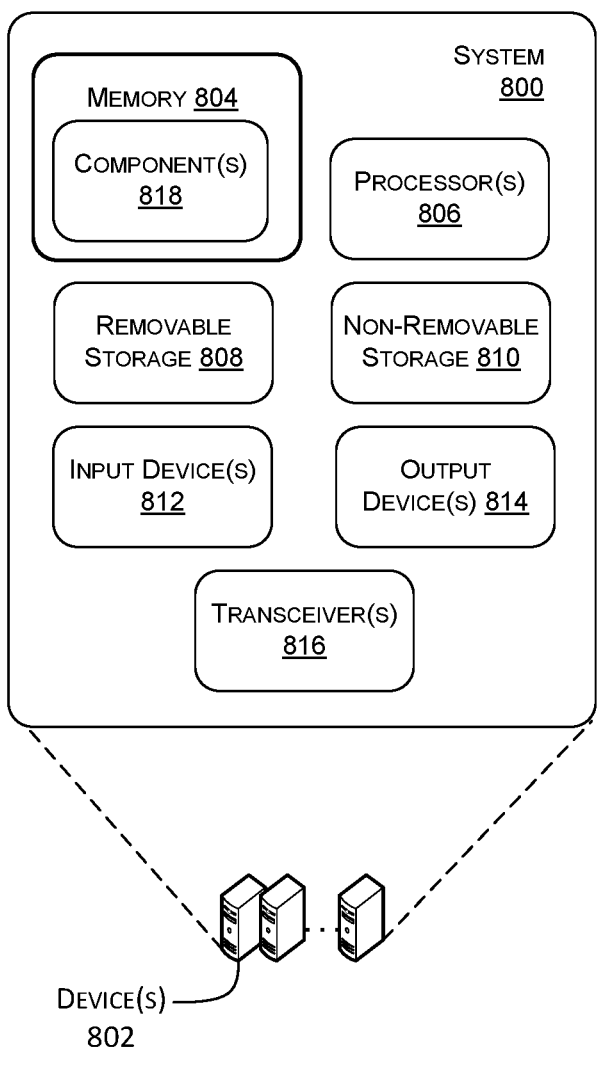
FIG. 8 illustrates an example of a system configured to perform various functions described herein.

FIG. 8 illustrates an example of a system 800 configured to perform various functions described herein. In various implementations, the system 800 is implemented by one or more computing devices 801, such as servers. The system 800 includes any of memory 804, processor(s) 806, removable storage 808, non-removable storage 810, input device(s) 812, output device(s) 814, and transceiver(s) 816. The system 800 may be configured to perform various methods and functions disclosed herein.

The memory 804 may include component(s) 818. The component(s) 818 may include at least one of instruction(s), program(s), database(s), software, operating system(s), etc. In some implementations, the component(s) 818 include instructions that are executed by processor(s) 806 and/or other components of the system 800. For example, the component(s) 818 include instructions for executing functions of a surgical robot (e.g., the surgical robot 112), a console (e.g., the console 114), a monitor (e.g., the monitor 116), an augmentation system (e.g., the augmentation system 118), or any combination thereof.

In some embodiments, the processor(s) 806 include a central processing unit (CPU), a graphics processing unit (GPU), or both CPU and GPU, or other processing unit or component known in the art.

The system 800 may also include additional data storage devices (removable and/or non-removable) such as, for example, magnetic disks, optical disks, or tape. Such additional storage is illustrated in FIG. 8 by removable storage

808 and non-removable storage 810. Tangible computer-readable media can include volatile and non-volatile, removable and non-removable media implemented in any method or technology for storage of information, such as computer readable instructions, data structures, program modules, or other data. The memory 804, the removable storage 808, and the non-removable storage 810 are all examples of computer-readable storage media. Computer-readable storage media include, but are not limited to, Random Access Memory (RAM), Read-Only Memory (ROM), Electrically Erasable Programmable Read-Only Memory (EEPROM), flash memory, or other memory technology, Compact Disk Read-Only Memory (CD-ROM), Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the system 800. Any such tangible computer-readable media can be part of the system 800.

The system 800 may be configured to communicate over a communications network using any common wireless and/or wired network access technology. Moreover, the system 800 may be configured to run any compatible device Operating System (OS), including but not limited to, Microsoft Windows Mobile, Google Android, Apple iOS, Linux Mobile, as well as any other common mobile device OS.

The system 800 also can include input device(s) 812, such as a keypad, a cursor control, a touch-sensitive display, voice input device, etc., and output device(s) 814 such as a display, speakers, printers, etc. In some cases, the input device(s) 812 include at least one of controls (e.g., the controls 124 described above with reference to FIG. 1), a scope (e.g., a scope included in the tools 110 described above with reference to FIG. 1), or sensors (e.g., sensors included in the surgical robot 112 and/or tools 110 of the surgical robot 112). In some examples, the output device(s) 814, include at least one display (e.g., the console display 122 and/or the monitor display 126), a surgical robot (e.g., the surgical robot 112), arms (e.g., arms 120), tools (e.g., the tools 110), or the like.

As illustrated in FIG. 8, the system 800 also includes one or more wired or wireless transceiver(s) 816. For example, the transceiver(s) 816 can include a network interface card (NIC), a network adapter, a Local Area Network (LAN) adapter, or a physical, virtual, or logical address to connect to various network components, for example. To increase throughput when exchanging wireless data, the transceiver(s) 816 can utilize multiple-input/multiple-output (MIMO) technology. The transceiver(s) 816 can comprise any sort of wireless transceivers capable of engaging in wireless (e.g., radio frequency (RF)) communication. The transceiver(s) 816 can also include other wireless modems, such as a modem for engaging in Wi-Fi, WiMAX, Bluetooth, infrared communication, and the like. The transceiver(s) 816 may include transmitter(s), receiver(s), or both.

Example 1—Sample Process for Identifying Bleeding in a Surgical Scene

Figure 9:
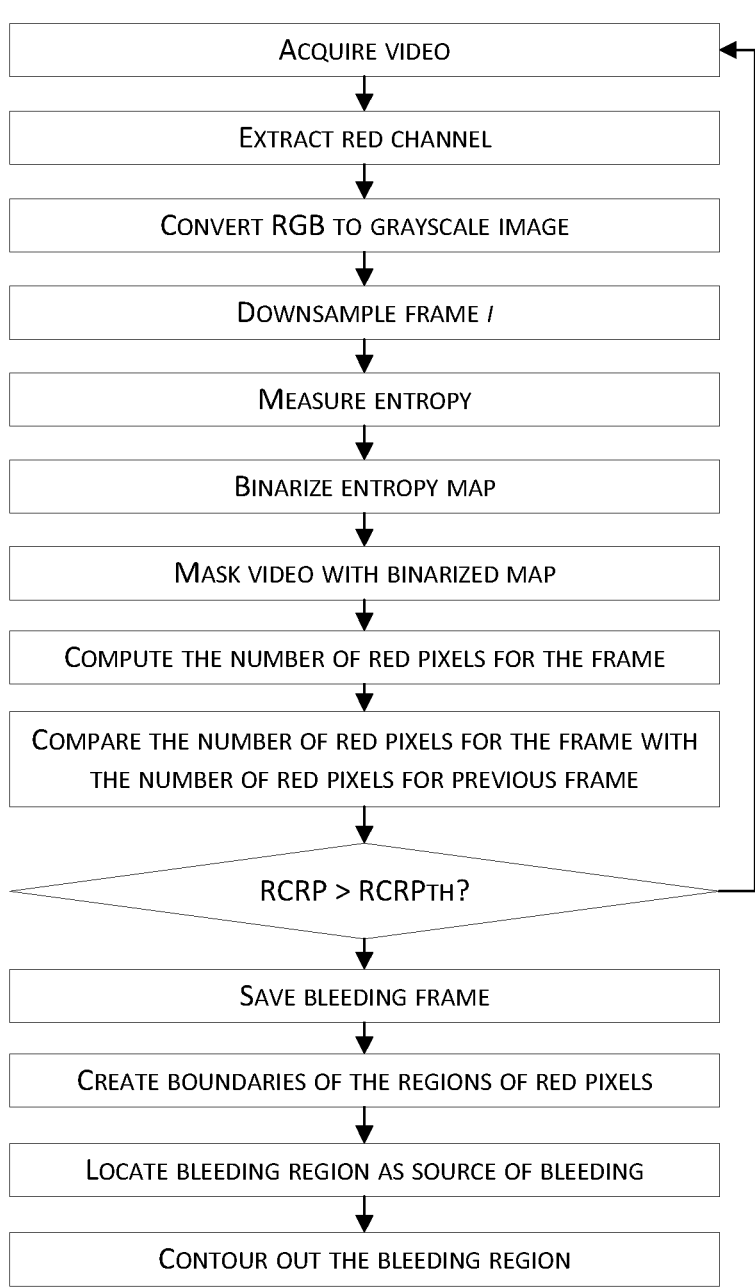
FIG. 9 illustrates a flow chart of a sample process that can be used to identify and locate bleeding, such as arterial bleeding.

FIG. 9 illustrates a flow chart of a sample process that can be used to identify and locate bleeding, such as arterial bleeding. The problem of bleeding detection is modeled as random movement detection. In Example 1, the uniformity of different regions of a video frame was performed based on concept on entropy Example 1 describes a process that can be used to monitor a surgical scene, detect arterial bleeding and abrupt changes in the scene, and localize and contour the source of bleeding. The process masks the down-sampled input frame from real-time video of the surgery scene with the map of local entropy, which enables blacking out everything in the masked region. Then, the number of red pixels within the masked image is counted, and the rate of change in the number of red pixels acts as a signal for identifying the frame of arterial bleeding and localizing its source. The core of the process is based on counting the number of red pixels within the local entropy map for each frame.

A local entropy mask for a surgery scene includes of two types of pixels: high-entropy pixels that belong to tissues and low-entropy pixels which can represent the presence of blood due to arterial bleeding. To detect the moment of arterial bleeding, the number of red pixels on the masked RGB image are counted and compared with the number of red pixels associated with the previous frame. The change in the local entropy map is used as a mechanism to detect the moment of bleeding. Furthermore, after identifying the moment of arterial bleeding, the process can localize the source as well, which can help the surgeon to control the bleeding faster. This can prevent dramatic changes in the surgery scene and the occurrence of red-out situations. The process of Example 1 can be utilized as an artificial vision system to predict and prevent severe bleeding circumstances during robotic surgery.

Example 2—Results of the Sample Process of Example 1

Example 2 provides a validation study of the process described in Example 1. As shown in Example 2, the process can be used to detect the moment of bleeding within an average of 0.635 seconds of its occurrence with the recorded test videos. In addition, it can be used to locate the source of arterial bleeding with 97.5% accuracy with respect to its true location. Furthermore, Example 2 includes a discussion of other methods that may be utilized to prevent the occurrence of red-out situations and the resulting occlusion of the surgery scene, which could help surgeons manage and control red-out situations and, consequently, prevent damage to patients' tissues and organs.

Figure 10A:
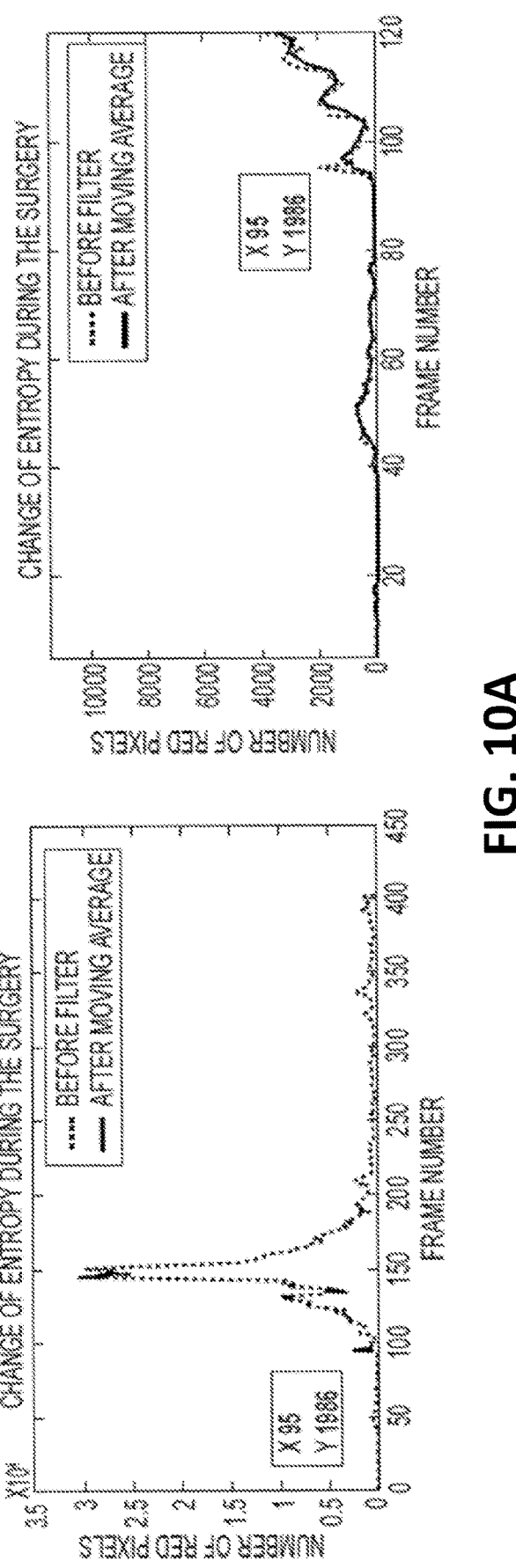
FIG. 10A depicts the changes in entropy over time (per-frame) within a prerecorded video with arterial bleeding.

In this section, the accuracy and robustness of the process described in Example 1 is analyzed. A robotic surgery scene was recorded using a stereoscopic camera during laparoscopic surgery. During the surgery, two types of bleeding can occur: venous and arterial bleeding. The process detects arterial bleeding, so a dataset that included 20 videos with occurrences of arterial bleeding was collected. The process described in Example 1 was applied to this dataset, which yielded an output of the frame number of the bleeding detection and the location of the source of the arterial bleeding. The true frame and source of the arterial bleeding was identified manually after importing the recorded video into the video editing software. FIGS. 10A and 10B show a result of Example 2 following import into video-editing software.

The hypotheses were run on recorded videos from robotic surgeries for testing purposes. Within the robotic surgery scenes, it is possible to recognize the moment and location of the initial arterial bleeding through observation. This type of observation can be quantified using the frame number of the initial arterial bleeding and the region of interest by importing the video into software designed for video editing. In this scenario, the recorded robotic surgery videos were passed through as inputs to the process described in Example 1, allowing a comparison of the output of the process with the true frame number and exact location of arterial bleeding, which was determined through observation using the video editing software. In order to measure the accuracy of this solution, the frame number and location of the arterial bleeding from this process were compared with the frame number and location of the arterial bleeding from the video editing software, which were found based on user observation. These two tactics were used to measure the accuracy of the process, e.g., using Equations 6 and 7.

FIG. 10B illustrates localization of a region of arterial bleeding within a video scene. The location of the source of arterial bleeding is outlined.

$$\text{Detection Error} = \frac{\begin{array}{c}|\text{Actual Arterial Bleeding Frame} - \\ \text{Computed Arterial Frame}|\end{array}}{\text{Frame Rate of Video}} \qquad \text{Eq. 6}$$

$$\% \text{ of Localization Max Error} = \sqrt{\frac{(x_r - x_c)^2 + (y_r - y_c)^2}{w^2 + h^2}} * 100 \qquad \text{Eq. 7}$$

In order to realize the hypotheses, a process to monitor and record the robotic surgery scene in real time was developed. The process described in Example 1 was used to measure the local and temporal entropy of the video, detect arterial bleeding, localize its source, and record the video frame of the beginning of arterial bleeding and occurrence of spread of blood. The inputs to this process were the video frames from the robotic surgery scene, and the output was the number of the video frame in which the arterial bleeding started and the location of the source of the arterial bleeding. Then, the robotic surgery video was imported into the video editing software which allows us to review the video frames to determine the exact frame number in which arterial bleeding occurred.

In Equation 7, $x_r$ is the horizontal location of the true location of arterial bleeding, which is identified by the observer though the video editing software. $y_r$ is the vertical location of the true location of arterial bleeding, which is also identified by the observer though the video editing software. $x_c$ is the computed horizontal location of the centroid of arterial bleeding region at the moment of detection, and $y_c$ is the computed horizontal location of the centroid of arterial bleeding region at the moment of detection. w and h are the width and height of the video, respectively. Because every video has its own size, the localization error is divided by $w^2 \pm h^2$ for the sake of normalization.

TABLE 1

| The result of running the process of Example 1 on 10 prerecorded videos | | | | | |
|---|---|---|---|---|---|
| Video Set # | Actual Arterial Bleeding Frame | Computed Arterial Frame | Detection Error (seconds) | Localization Error (pixels) | % of max Error |
| 1 | 94 | 95 | 0.04 | 30 | 2.04 |
| 2 | 230 | 238 | 0.16 | 36 | 2.45 |
| 3 | 329 | 350 | 0.7 | 78 | 5.31 |
| 4 | 160 | 170 | 0.33 | 27 | 1.84 |
| 5 | 401 | 440 | 1.3 | 32 | 2.18 |
| 6 | 109 | 94 | 0.5 | 30 | 2.04 |
| 7 | 209 | 220 | 0.36 | 43 | 2.93 |
| 8 | 371 | 410 | 1.3 | 30 | 2.04 |

TABLE 1-continued

| The result of running the process of Example 1 on 10 prerecorded videos | | | | | |
|---|---|---|---|---|---|
| Video Set # | Actual Arterial Bleeding Frame | Computed Arterial Frame | Detection Error (seconds) | Localization Error (pixels) | % of max Error |
| 9 | 298 | 278 | 0.66 | 42 | 2.86 |
| 10 | 402 | 432 | 1 | 22 | 1.50 |

FIG. 10A depicts the temporal entropy within a prerecorded video with arterial bleeding. It can be seen that the first abrupt change in the number of red pixels in the entropy map occurred in frame 94. The right graph is the zoomed version of the left one in the neighborhood of frame number 94. It supports the hypothesis that the abrupt changes in the number of red pixels within the local entropy map can be used for the detection of arterial bleeding within the surgery scene.

The first abrupt change in the number of red pixels was observed in frame 95. The difference between the true value of the number of red pixels and the output of the moving average filter depicts a visualization of this abrupt change. This supports the hypothesis that the number of red pixels in the masked RGB frame with the entropy map can be used as an indicator and locator of the arterial bleeding in robotic surgery.

FIG. 10B depicts an area of bleeding detected in a prerecorded video.

Figure 11A:
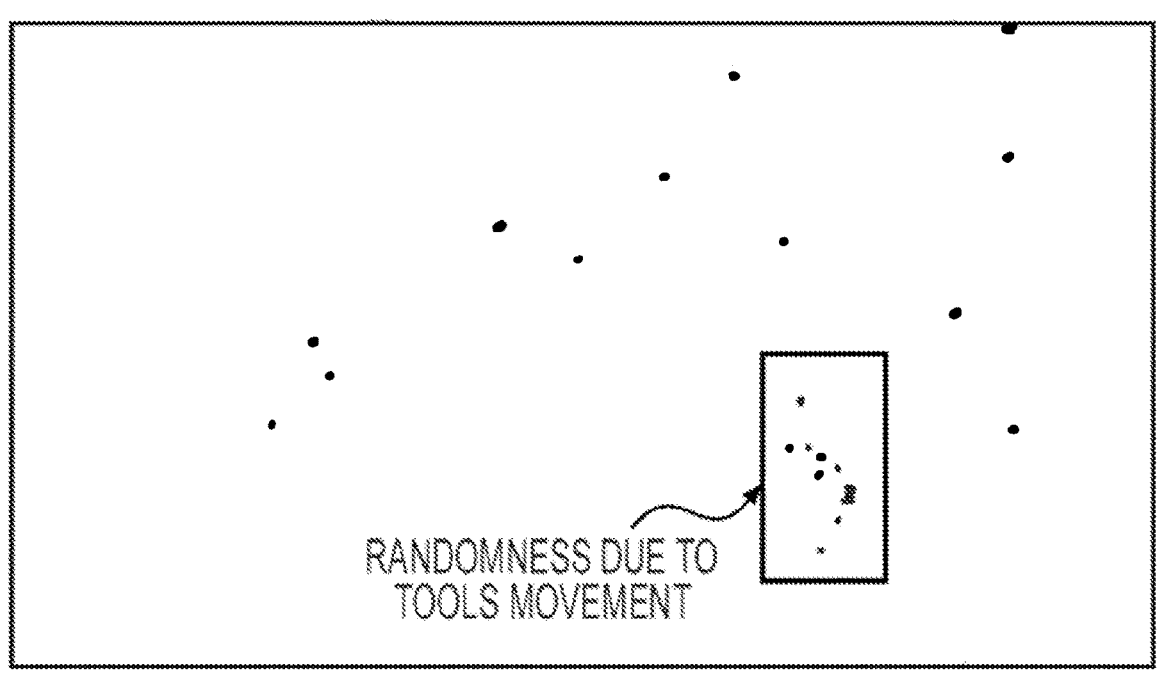
FIG. 11A depicts a frame based on an entropy map of a surgery scene before arterial bleeding.
Figure 11B:
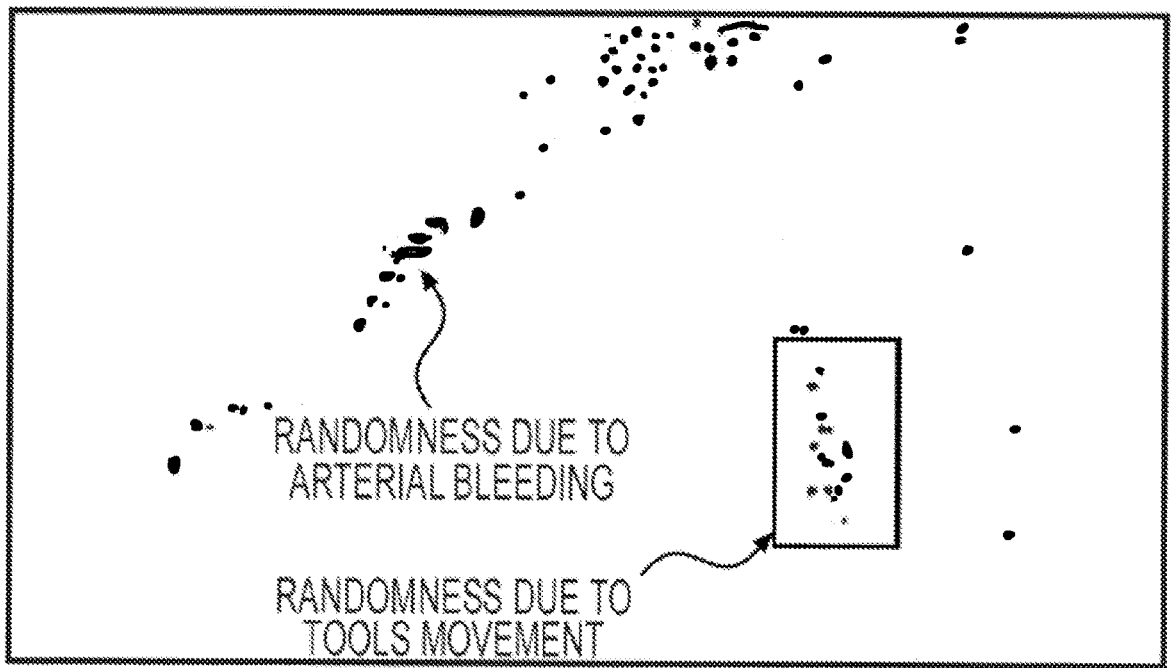
FIG. 11B depicts a frame based on an entropy map of a surgery scene at the moment of arterial bleeding, with as two types of pixels at the moment of arterial bleeding.

FIG. 11A depicts a masked frame of the surgery scene before arterial bleeding. The color of the pixels in the masked frame is white, which indicates that the source of the increase in entropy is not bleeding. FIG. 11B shows a masked frame with three types of pixels: high-entropy pixels that belong to tissues (depicted in white), pixels that represent tool movement (depicted in black), and pixels that represent the presence of blood due to arterial bleeding (depicted in gray).

FIG. 12 shows the entropy map of the surgery scene before arterial bleeding for one sample pre-recorded robotic surgery video. The color of some of the pixels in the entropy map is black, which indicates that the source of the increase in entropy is not bleeding. Further, FIG. 12 shows the two types of pixels: pixels that belong to tissues (shown in white) and pixels which represent the presence of blood due to arterial bleeding (shown in gray).

FIG. 12 includes two images demonstrate the effect of arterial bleeding on the change in the ratio of red pixels within the surgery scene. Within the entropy map, the randomness introduced to the scene by the movement of surgical tools, and the arterial bleeding represents the increase in local entropy can be distinguished. FIG. 12 demonstrates the effect of arterial bleeding on the change in the ratio of low-entropy red pixels within the surgery scene. In addition, as mentioned earlier, the process can be used to contour the bleeding region and localize the source of arterial bleeding.

FIG. 13 shows how the process of Example 1 can be used to contour regions with a change in local entropy and label them. These two pictures show the process of contouring before arterial bleeding occurred. In the right image, there are few regions of interest in the context of change in entropy, while the area of interest is expanded in the right picture, and there are more regions that are recognized and contoured by the process. FIG. 13 demonstrates the ability of the process to localize the cause of arterial bleeding due to the change in entropy introduced by a surgeon and surgical tools.

Figure 14:
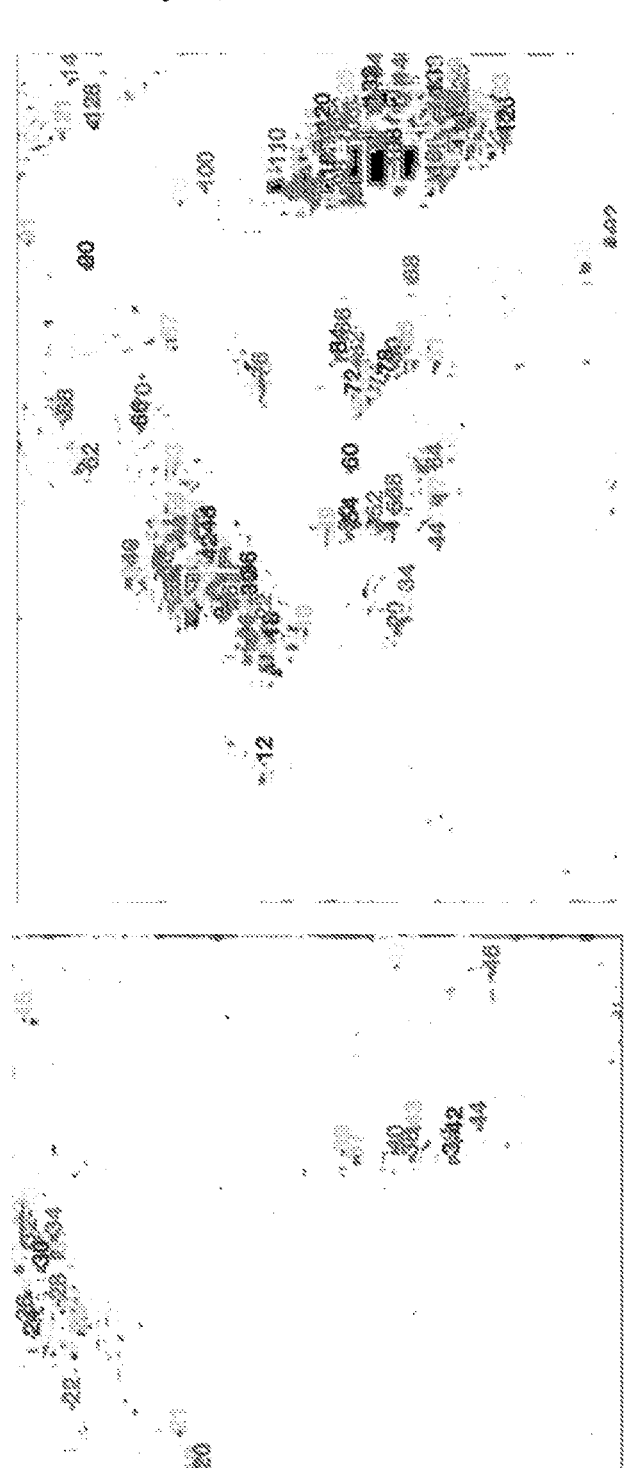
FIG. 14 shows how the process of Example 1 can be used to contour regions with a change in local entropy and label them.

FIG. 14 shows how the process of Example 1 can be used to contour regions with a change in local entropy and labels them. These two pictures show the process of contouring after arterial bleeding occurred. In the left image, there are few regions of interest in the context of change in entropy, while the area of interest is expanded in the right picture, and there are more regions that are recognized and contoured by the process. FIG. 14 depicts the capability of the process to locate the source of arterial bleeding and the regions of bleeding.

FIG. 15 includes three images comparing the change in the Fourier Transform of the surgery scene. A comparison of the middle image with the bottom and top images, before and after arterial bleeding, shows that the vertical line appeared only at the moment of arterial bleeding, which occurred in the same frame in which the entropy of the video scene changed. FIG. 15 shows the change in the Fast Fourier Transform at the moment of arterial bleeding. The change in spatial frequency is a result of the sudden change of scene at the moment of arterial bleeding, which occurred in the same frame detected by the process of Example 1.

In this example, the process of Example 1 was evaluated based on its ability to detect the moment of arterial bleeding within the recorded video and to identify the source of arterial bleeding and its location and overlay it on the original video.

Further, the accuracy of the process in detecting the moment of arterial bleeding based on the difference between the arterial bleeding frame according to the process and its true frame was evaluated. To identify the true frame of arterial bleeding, the videos were important into the video editing software to and the frames were observed. After adding the video to the timeline of the video editing software, it was possible to scroll through the video by individual frame until arterial bleeding was observed (manually). The timeline indicator shows the elapsed seconds and frame number, giving the information needed to compute the total number of frames elapsed based on the frame rate of the video:

$$\text{Frame Arterial Bleeding} = (\text{Seconds} * \text{Video Frame Rate}) \pm \text{Frame Number} \qquad \text{Eq. 8}$$

Figure 16:
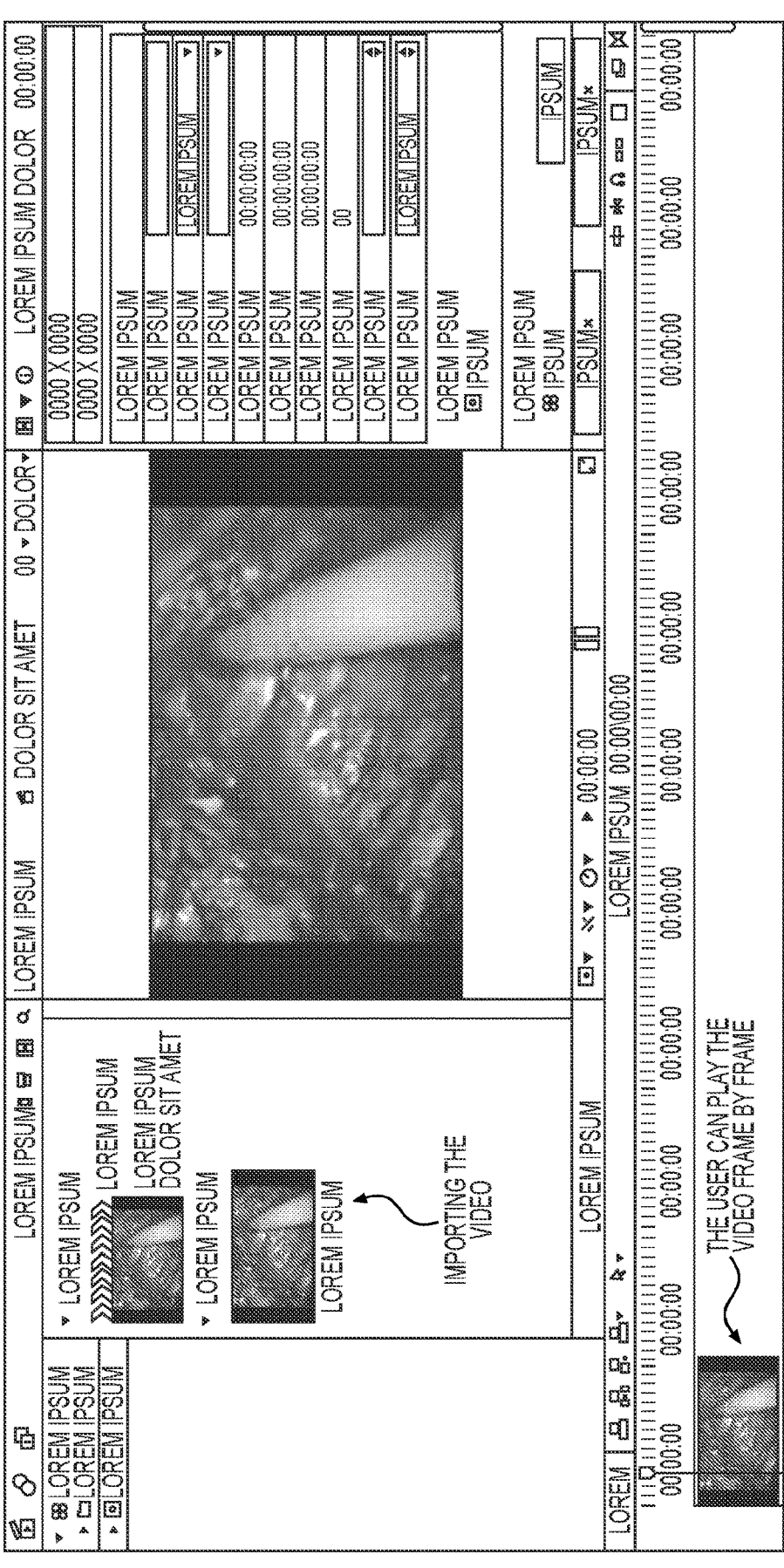
FIG. 16 illustrates an example of a technique for importing the recorded video into video editing software.

FIG. 16 illustrates an example of a technique for importing the recorded video into the video editing software. The source of arterial bleeding was localized by moving the mouse over the location of arterial bleeding and clicking to obtain the x and y coordinates. These values were compared with the arterial bleeding coordinates obtained by the process of Example 1. The origin of arterial bleeding localized in the process is based on the region with the highest area of red pixels. This area was used as an indicator for the origin of arterial bleeding and compared the Cartesian distance to compute the error.

In this section, different aspects of the process of Example 1 are discussed in relation to the improvement of accuracy, performance, and robustness. This provides a guide for future work for improving the process for other applications during robotic surgery.

Abrupt changes in the robotic operating scene can be used to identify and localize arterial bleeding. Example 2 illustrates the results of applying the process of Example 1 to ten, gathered, recorded videos of intraoperative robotic surgeries that show that the occurrence of arterial bleeding leads to sudden changes within the robotic surgery scene. This abrupt change is due to the sudden release of blood caused by cutting the arterial vessel during surgery. Example 2 shows that abrupt changes within the surgical scene can be detected by measuring the information encoded within the different regions of the individual video frames. Specifically, this change in information can be used to detect arterial bleeding, or any other type of bleeding that produces an abrupt change in entropy within the surgical scene.

The size of the neighborhood for computing the local entropy and generating the entropy map affects the accuracy of the process of Example 1. A window size that is too small can result in an imprecise estimate of local entropy because of the lack of sampling, while a window size that is too large can result in a loss of localization. Grazzini, J., et al., *OBJECT RECOGNITION SUPPORTED BY USER INTER-ACTION FOR SERVICE ROBOTS.* 2002. IEEE. Increasing the size of the neighborhood affects the computational cost of the process and makes the procedure less efficient. An optimization algorithm based on the computed error could be used to accurately train the algorithm for the appropriate neighborhood size. Moreover, different types of surgeries might have different optimal parameters.

Down-sampling and smoothing the input video frame enhance the efficiency of the process of Example 1 in terms of speed by decreasing the degree of complexity of the input matrix. The ratio of down-sampling is not unbounded and cannot exceed a certain value. Although decreasing the degree of smoothing beyond the ratio of one-half makes the process work faster, its cost compromises the accuracy of the process for detecting the frame of arterial bleeding as well its location. Its impact on the accuracy of localizing the source of arterial bleeding is greater than its effect on the detection of the frame of arterial bleeding. Besides its effect on improving the speed of process, reasonable smoothing with a ratio less than one-half, down-sampling significantly improves the robustness of the process. This smoothing eliminates noise and decreases the likelihood of false detection on the edges formed by the noise.

As a broader application, the process could be used to warn surgeons about accidental tool and/or camera movement, which could lead to tissue damage in the patient. The process can be used in the design of predictive and preventive systems for managing hemorrhaging during robotic surgery. It can be crucial to have an artificial vision system that can monitor the movements of surgical tools and warn surgeons about their abrupt movement of surgical instruments. It can also predict the likelihood of sudden bleeding. The process is capable of this because, as we observed, there is a correlation between the sudden movement of a surgical tool and the occurrence of arterial bleeding. Since the process can distinguish between change in local entropy of the scene introduced by the abrupt movement of surgical instruments and/or the camera, it can be exploited as a warning mechanism to notify surgeons about the way in which they move the surgical tools. Such warnings could prevent the occurrence of bleeding. Furthermore, the process can be utilized to improve the learning curve for new surgeons by informing their movements and increasing their dexterity.

Example 2 shows that computing the spatiotemporal, computing local entropy of the image frame by frame, can be used as an effective approach to detect the occurrence of a red-out and blood blockage of the surgery scene and to help manage and control red-out circumstances and thereby prevent severe damage to patients' tissues and organs. Example 2 describes a systematic way to measure the accuracy and robustness of the process for different sets of videos. The accuracy is measured by comparing the outputs of the process with the arterial frame number and location detected through observation of the recorded test video after it is imported into video editing software.

Example Clauses

A. A method, including: identifying a first frame depicting a surgical scene; identifying a second frame depicting the surgical scene; identifying whether the second frame depicts bleeding by analyzing the first frame and the second frame; and outputting the second frame with an augmentation indicating whether bleeding is depicted in the second frame.

B. The method of clause A, further including: outputting third frames depicting bleeding in the surgical field with augmentations indicating the bleeding, a video of the surgical scene including the first frame, the second frame, and the third frames.

C. The method of clause A or B, wherein the first frame depicts the surgical scene at a first time and the second frame depicts the surgical scene at a second time, the first time occurring before the second time.

D. The method of any one of clauses A to C, wherein the surgical scene is at least one of a laparoscopic surgical scene, an endoscopic surgical scene, or an open surgical scene.

E. The method of any one of clauses A to D, wherein a depiction of the bleeding is absent from the first frame.

F. The method of any one of clauses A to E, wherein identifying whether the second frame depicts bleeding includes determining, by a trained machine learning model, whether the second frame depicts bleeding.

G. The method of any one of clauses A to F, wherein identifying whether the second frame depicts bleeding includes performing at least one of clustering, motion analysis, or texture analysis on the first frame and the second frame.

H. The method of any one of clauses A to G, wherein identifying whether the second frame depicts bleeding includes: generating a first entropy map representing local entropies of first pixels in the first frame; generating a second entropy map representing local entropies of second pixels in the second frame; and determining whether the second frame depicts bleeding based on the first entropy map and the second entropy map.

I. The method of clause H, wherein generating the first entropy map includes applying an entropy kernel to the first frame; and wherein generating the second entropy map includes applying the entropy kernel to the second frame.

J. The method of clause I, wherein applying the entropy kernel to the first frame includes convolving the entropy kernel with a first detection window of the first frame, and wherein applying the entropy kernel to the second frame includes convolving the entropy kernel with a second detection window of the second frame.

K. The method of any one of clauses H to J, wherein generating the first entropy map includes: calculating a first local entropy of a first pixel in the first frame by convolving a first detection window with the entropy kernel, the first frame including the first detection window, the first detection window including the first pixel; generating a first entropy pixel by comparing the first local entropy to a first threshold, a first value of the first entropy pixel being a first level or a second level based on whether the first local entropy is less than the first threshold; and generating the first entropy map to include the first entropy pixel, and wherein generating the second entropy map includes: calculating a second local entropy of a second pixel in the second frame by convolving a second detection window with the entropy kernel, the second frame including the second detection window, the second detection window including the second pixel; generating a second entropy pixel by comparing the second local entropy to the first threshold, a second value of the first entropy pixel being the first level or the second level based on whether the second local entropy is less than the first threshold; and generating the second entropy map to include the second entropy pixel.

L. The method of clause K, further including setting the first threshold based on a user input.

M. The method of any one of clauses H to L, wherein the first entropy map is a first binary image and the second entropy map is a second binary image.

N. The method of any one of clauses H to M, wherein determining whether the second frame depicts bleeding based on the first entropy map and the second entropy map includes: generating a first masked frame by performing pixel-by-pixel multiplication of the first entropy map and the first frame; identifying a first number of nonzero pixels in the first masked frame; generating a second masked frame by performing pixel-by-pixel multiplication of the second entropy map and the second frame; identifying a second number of nonzero pixels in the second masked frame; and determining whether the second frame depicts bleeding by comparing the first number and the second number.

O. The method of clause N, wherein comparing the first number and the second number includes: generating a difference by subtracting the first number from the second number; and comparing the difference to a second threshold.

P. The method of clause O, further including setting the second threshold based on a user input.

Q. The method of any one of clauses N to P, wherein determining whether the second frame depicts bleeding by comparing the first number and the second number includes: determining a first pixel ratio by dividing the first number by a total number of pixels in the first frame; determining a second pixel ratio by dividing the second number by a total number of pixels in the second frame; and determining whether the second frame depicts bleeding by comparing the first pixel ratio and the second pixel ratio.

R. The method of clause Q, wherein comparing the first pixel ratio and the second pixel ratio includes: generating a difference by subtracting the first pixel ratio from the second pixel ratio; and comparing the difference to a second threshold.

S. The method of clause R, further including setting the second threshold based on a user input.

T. The method of any one of clauses H to S, further including: generating a first filtered frame by filtering the first frame; and generating a second filtered frame by filtering the second frame, wherein the first entropy map is generated based on the first filtered frame and the second entropy map is generated based on the second filtered frame.

U. The method of any one of clauses A to T, further including converting the first frame and the second frame from 3-channel RGB images to single-channel grayscale images.

V. The method of any one of clauses A to U, wherein the first frame includes a red channel of a first image of the surgical scene, and wherein the second frame includes a red channel of a second image of the surgical scene.

W. The method of any one of clauses A to V, wherein the first frame and the second frame are identified in multiple frames of a video, and wherein the first frame and the second frame are nonconsecutive frames in the video.

X. The method of any one of clauses A to W, wherein identifying whether the second frame depicts bleeding includes determining that the second frame depicts the bleeding.

Y. The method of clause X, wherein outputting the second frame with the augmentation includes: outputting a visual overlay on the second frame indicating the bleeding.

Z. The method of clause X or Y, wherein outputting the second frame with the augmentation includes: outputting an audio signal and/or a haptic signal simultaneously with outputting the second frame, the audio signal and/or the haptic signal indicating the bleeding.

AA. The method of any one of clauses X to Z, wherein outputting the second frame with the augmentation includes: identifying a portion of the first frame depicting a physiological structure obscured by the bleeding in the second frame, the first frame depicting the physiological structure without the bleeding; and outputting the augmentation as a visual overlay of the second frame, the augmentation including the portion of the first frame.

AB. The method of clause AA, wherein the visual overlay is overlaid on a region of the second frame that depicts the bleeding.

AC. The method of clause AA or AB, wherein the visual overlay is overlaid in a region of the second frame that omits the bleeding.

AD. The method of any one of clauses A to AC, wherein the first frame depicts the surgical scene at a first time and the second frame depicts the surgical scene at a second time, the second time occurring within a threshold interval after the first time.

AE. The method of any one of clauses X to AD, further including: determining a location of the source of the bleeding.

AF. The method of clause AE, wherein determining the location of the source of the bleeding includes: identifying a region of the second frame depicting red pixels corresponding to less than a first threshold of local entropies, the region including a cluster of the red pixels; and determining that the location of the source of the bleeding is within the region.

AG. The method of clause AE or AF, wherein determining the location of the source of the bleeding includes determining a centroid of the region, the region being a largest cluster of red pixels corresponding to less than the first threshold of local entropies in the second frame.

AH. The method of any one of clauses AE to AG, wherein outputting the second frame with the augmentation includes outputting an indication of the location of a source of the bleeding.

AI. The method of any one of clauses A to AH, further including: generating the augmentation based on at least one of a preoperative image or an intraoperative image.

AJ. The method of any one of clauses X to AI, further including: determining a magnitude of the bleeding, a flow rate of the bleeding, a velocity of the bleeding, a type of the bleeding, or a combination thereof.

AK. The method of clause AJ, wherein determining the magnitude of the bleeding includes: identifying a region of the second frame depicting red pixels corresponding to greater than a first threshold of local entropies and red values greater than a threshold red value, the region including a cluster of the red pixels; and determining the magnitude of the bleeding based on an area of the region.

AL. The method of claim any one of AE to AK, wherein outputting the second frame with the augmentation includes outputting an indication of the magnitude of the bleeding.

AM. A system, including: at least one processor; and memory storing instructions that, when executed by the at least one processor, cause the system to perform operations including: the method of any one of clauses A to AL.

AN. The system of clause AM, further including: a scope configured to obtain the first frame and the second frame.

AO. The system of clause AM or AN, further including: a display configured to output the first frame and the second frame.

AP. The system of any one of clauses AM to AO, wherein the system is a robotic surgical system.

AQ. The robotic system of clause AP, further including: a tool including at least one sensor, wherein the operations further include: receiving, from at least one sensor, a feedback signal indicating that the tool has touched a physiological structure, and wherein identifying whether the second frame depicts bleeding includes determining that the second frame depicts bleeding based on the feedback signal.

AR. The robotic system of clause AP or AQ, further including: a tool including a 3-dimensional (3D) scanner, wherein the operations further include: receiving, from the 3D scanner, volumetric data depicting the surgical scene.

AS. The robotic system of any one of clauses AP to AR, further including: a tool including a camera configured to capture the first frame and the second frame, wherein the operations further include: causing the tool to reposition based on whether the second frame depicts bleeding.

AT. The robotic system of any one of clauses AP to AS, further including: one or more tools configured to stop the bleeding, wherein the operations further include causing the one or more tools to stop the bleeding in the surgical scene.

AU. The system of any one of clauses AM to AT, further including: a console configured to control one or more surgical tools, the one or more surgical tools including a scope configured to obtain the first frame and the second frame.

AV. The system of clause AU, wherein the console includes one or more controls configured to receive an input from a user, the console controlling the one or more surgical tools based on the input.

AW. The system of clause AV, wherein the includes a display configured to output the first frame and the second frame.

AX. A non-transitory computer-readable storage medium encoding instructions to perform the method of any one of clauses A to AL.

AY. A robotic surgical system, including: a camera configured to capture a video of a surgical scene; an output device configured to display the video; at least one processor; and memory storing instructions that, when executed by the at least one processor, cause the system to perform operations including: identifying a first frame in the video; identifying a second frame in the video; identifying that the second frame depicts bleeding by: determining a ratio of low-entropy red pixels in the first frame, the low-entropy red pixels in the first frame including pixels in the first frame with entropy levels over a first threshold and red channel values over a second threshold; determining a ratio of low-entropy red pixels in the second frame, the low-entropy red pixels in the second frame including pixels in the second frame with entropy levels over the first threshold and red channel values over the second threshold; and determining that a difference between the ratio of low-entropy pixels in the second frame and the ratio of low-entropy red pixels in the second frame is greater than a third threshold; and based on identifying that the second frame depicts the bleeding, causing the output device to display the second frame with an augmentation indicating the bleeding.

AZ. The robotic surgical system of clause AY, including: a console configured to control surgical tools, the surgical tools including: a scope including the camera; the output device; and an input device configured to receive an input from the user, the console controlling the surgical tools based on the input.

BA. The robotic surgical system of clause AY or AZ, wherein determining the ratio of low-entropy red pixels in the first frame includes: generating a first entropy mask representing local entropies of the pixels in the first frame by convolving an entropy kernel with a first detection window of the first frame; generating a first masked frame by performing pixel-by-pixel multiplication of the first entropy mask and the first frame; and identifying a number of pixels in the first masked frame with red channel values over the second threshold, and wherein determining the ratio of low-entropy red pixels in the second frame includes: generating a second entropy mask representing local entropies of the pixels in the second frame by convolving the entropy kernel with a second detection window of the second frame; generating a second masked frame by performing pixel-by-pixel multiplication of the second entropy mask and the second frame; and identifying a number of pixels in the second masked frame with red channel values over the second threshold.

CONCLUSION

As will be understood by one of ordinary skill in the art, each embodiment disclosed herein can comprise, consist essentially of or consist of its particular stated element, step, or component. Thus, the terms "include" or "including" should be interpreted to recite: "comprise, consist of, or consist essentially of." As used herein, the transition term "comprise" or "comprises" means has, but is not limited to, and allows for the inclusion of unspecified elements, steps, or components, even in major amounts. The transitional phrase "consisting of" excludes any element, step, or component not specified. The transition phrase "consisting essentially of" limits the scope of the embodiment to the specified elements, steps, or components and to those that do not materially affect the embodiment. The term "based on" should be interpreted as "based at least partly on," unless otherwise specified.

Unless otherwise indicated, all numbers expressing quantities of properties used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing this disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the present disclosure otherwise claimed. No language in the specification should be construed as indicating any non-claimed element essential to the practice of the techniques described herein.

Groupings of alternative elements or implementations disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors. Of course, variations on these described embodiments will become apparent to those of ordinary skill in the art upon reading the foregoing description. The inventor expects skilled artisans to employ such variations as appropriate, and the inventors intend for the techniques disclosed herein to be practiced otherwise than specifically described herein. Accordingly, the scope of the claims of this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

In closing, it is to be understood that the embodiments of the disclosure are illustrative of the principles of the present invention. Other modifications that can be employed are within the scope of the implementations described herein. Thus, by way of example, but not of limitation, alternative configurations of the present disclosure can be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings and/or examples making apparent to those skilled in the art how the several forms of the disclosure can be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition.

What is claimed is:

1. A robotic surgical system, comprising:
a camera configured to capture a video of a surgical scene;
an output device configured to display the video;
at least one processor; and
memory storing instructions that, when executed by the at least one processor, cause the system to perform operations comprising:
    identifying a first frame in the video;
    identifying a second frame in the video;
    identifying that the second frame depicts bleeding by:
        determining a ratio of low-entropy red pixels in the first frame, the low-entropy red pixels in the first frame comprising pixels in the first frame with entropy levels over a first threshold and red channel values over a second threshold;
        determining a ratio of low-entropy red pixels in the second frame, the low-entropy red pixels in the second frame comprising pixels in the second frame with entropy levels over the first threshold and red channel values over the second threshold; and
        determining that a difference between the ratio of low-entropy pixels in the second frame and the ratio of low-entropy red pixels in the second frame is greater than a third threshold; and
    based on identifying that the second frame depicts the bleeding, causing the output device to display the second frame with an augmentation indicating the bleeding.

2. The robotic surgical system of claim 1, comprising:
a console configured to control surgical tools, the surgical tools comprising:
    a scope comprising the camera;
    the output device; and
    an input device configured to receive an input from a user, the console controlling the surgical tools based on the input.

3. The robotic surgical system of claim 1, wherein determining the ratio of low-entropy red pixels in the first frame comprises:
    generating a first entropy mask representing local entropies of the pixels in the first frame by convolving an entropy kernel with a first detection window of the first frame;

generating a first masked frame by performing pixel-by-pixel multiplication of the first entropy mask and the first frame; and
identifying a number of pixels in the first masked frame with red channel values over the second threshold, and
wherein determining the ratio of low-entropy red pixels in the second frame comprises:
generating a second entropy mask representing local entropies of the pixels in the second frame by convolving the entropy kernel with a second detection window of the second frame;
generating a second masked frame by performing pixel-by-pixel multiplication of the second entropy mask and the second frame; and
identifying a number of pixels in the second masked frame with red channel values over the second threshold.

4. A method, comprising:
identifying a first frame depicting a surgical scene;
identifying a second frame depicting the surgical scene;
identifying whether the second frame depicts bleeding by analyzing the first frame and the second frame; and
outputting the second frame with an augmentation indicating whether bleeding is depicted in the second frame;
wherein identifying whether the second frame depicts bleeding comprises:
    generating a first entropy mask representing local entropies of first pixels in the first frame;
    generating a second entropy mask representing local entropies of second pixels in the second frame; and
    determining whether the second frame depicts bleeding based on the first entropy mask and the second entropy mask.

5. The method of claim 4, wherein generating the first entropy mask comprises applying an entropy kernel to the first frame; and
wherein generating the second entropy mask comprises applying the entropy kernel to the second frame.

6. The method of claim 5, wherein generating the first entropy mask comprises:
calculating a first local entropy of a first pixel in the first frame by convolving a first detection window with the entropy kernel, the first frame comprising the first detection window, the first detection window comprising the first pixel;
generating a first entropy pixel by comparing the first local entropy to a first threshold, a first value of the first entropy pixel being a first level or a second level based on whether the first local entropy is less than the first threshold; and
generating the first entropy mask to include the first entropy pixel, and wherein generating the second entropy mask comprises:
calculating a second local entropy of a second pixel in the second frame by convolving a second detection window with the entropy kernel, the second frame comprising the second detection window, the second detection window comprising the second pixel;
generating a second entropy pixel by comparing the second local entropy to the first threshold, a second value of the first entropy pixel being the first level or the second level based on whether the second local entropy is less than the first threshold; and
generating the second entropy mask to include the second entropy pixel.

7. The method of claim 5, wherein applying the entropy kernel to the first frame comprises convolving the entropy kernel with a first detection window of the first frame, and wherein applying the entropy kernel to the second frame comprises convolving the entropy kernel with a second detection window of the second frame.

8. The method of claim 4, wherein determining whether the second frame depicts bleeding based on the first entropy mask and the second entropy mask comprises:

generating a first masked frame by performing pixel-by-pixel multiplication of the first entropy mask and the first frame;

identifying a first number of red pixels in the first masked frame;

generating a second masked frame by performing pixel-by-pixel multiplication of the second entropy mask and the second frame;

identifying a second number of red pixels in the second masked frame; and determining whether the second frame depicts bleeding by comparing the first number and the second number.

9. The method of claim 4, wherein the first frame and the second frame are identified in multiple frames of a video, and wherein the first frame and the second frame are nonconsecutive frames in the video.

10. The method of claim 4, wherein identifying whether the second frame depicts bleeding comprises determining that the second frame depicts the bleeding.

11. The method of claim 10, wherein outputting the second frame with the augmentation comprises:

identifying a portion of the first frame depicting a physiological structure obscured by the bleeding in the second frame, the first frame depicting the physiological structure without the bleeding; and outputting the augmentation as a visual overlay of the second frame, the augmentation comprising the portion of the first frame.

12. The method of claim 10, further comprising:

determining a location of a source of the bleeding by:

identifying a region of the second frame depicting red pixels corresponding to less than a first threshold of local entropies, the region comprising a cluster of the red pixels; and determining that the location of the source of the bleeding is within the region.

13. The method of claim 10, further comprising:

determining a location of a source of the bleeding, wherein determining the location of the source of the bleeding comprises determining a centroid of a region, the region being a largest cluster of red pixels corresponding to less than a first threshold of local entropies in the second frame.

14. The method of claim 10, further comprising:

determining a magnitude of the bleeding by:

identifying a region of the second frame depicting red pixels corresponding to lower than a first threshold of local entropies and red values greater than a threshold red value, the region comprising a cluster of the red pixels; and determining the magnitude of the bleeding based on a change in an area of the region of the second frame and a corresponding area of a frame subsequent to the second frame.

15. A robotic surgical system, comprising:

a tool comprising at least one sensor configured to generate a feedback signal indicating that the tool has touched a physiological structure;

at least one processor; and memory storing instructions that, when executed by the at least one processor, cause the system to perform operations comprising:

identifying a first frame depicting a surgical scene;

identifying a second frame depicting the surgical scene;

identifying whether the second frame depicts bleeding by analyzing the first frame and the second frame and further based on the feedback signal; and outputting the second frame with an augmentation indicating whether bleeding is depicted in the second frame.

16. The robotic surgical system of claim 15, further comprising:

a scope configured to obtain the first frame and the second frame; and/or a display configured to output the first frame and the second frame.

17. The robotic surgical system of claim 16, further comprising: a tool comprising a 3-dimensional (3D) scanner, wherein the operations further comprise: receiving, from the 3D scanner, volumetric data depicting the surgical scene.

18. The robotic surgical system of claim 16, further comprising: a tool comprising a camera configured to capture the first frame and the second frame, wherein the operations further comprise: causing the tool to reposition based on whether the second frame depicts bleeding.

19. The robotic surgical system of claim 16, further comprising: one or more tools configured to stop the bleeding, wherein the operations further comprise causing the one or more tools to stop the bleeding in the surgical scene.

20. The robotic surgical system of claim 15, further comprising a console configured to control one or more surgical tools, the one or more surgical tools comprising a scope configured to obtain the first frame and the second frame.

* * * * *